United States Patent
Dorando

(10) Patent No.: US 10,893,808 B2
(45) Date of Patent: Jan. 19, 2021

(54) INTERFACE DEVICES, SYSTEMS, AND METHODS FOR USE WITH INTRAVASCULAR PRESSURE MONITORING DEVICES

(71) Applicant: Volcano Corporation, San Diego, CA (US)

(72) Inventor: Dale Dorando, Shingle Springs, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 501 days.

(21) Appl. No.: 14/212,515

(22) Filed: Mar. 14, 2014

(65) Prior Publication Data

US 2014/0276142 A1    Sep. 18, 2014

Related U.S. Application Data

(60) Provisional application No. 61/790,755, filed on Mar. 15, 2013.

(51) Int. Cl.
*A61B 5/02* (2006.01)
*A61B 5/0215* (2006.01)
(Continued)

(52) U.S. Cl.
CPC ........ *A61B 5/02007* (2013.01); *A61B 5/0215* (2013.01); *A61B 5/02158* (2013.01);
(Continued)

(58) Field of Classification Search
CPC ..... A61B 5/0215; A61B 5/6851; A61B 5/026; A61B 5/02158; A61B 5/6852;
(Continued)

(56) References Cited

U.S. PATENT DOCUMENTS

| 5,111,041 A | 5/1992 | Imai |
| 5,233,999 A | 8/1993 | Dellacorna |

(Continued)

FOREIGN PATENT DOCUMENTS

| EP | 2276395 A2 | 1/2011 |
| GB | 2479340 A | 10/2011 |

(Continued)

OTHER PUBLICATIONS

International Search Report and Written Opinion Patent Cooperation Treaty Application No. PCT/US2014/026521, dated Jul. 3, 2014, 11 pages.

(Continued)

*Primary Examiner* — Christian Jang
*Assistant Examiner* — Karen E Toth

(57) ABSTRACT

Embodiments of the present disclosure are configured to assess the severity of a blockage in a vessel and, in particular, a stenosis in a blood vessel. In some particular embodiments, the devices, systems, and methods of the present disclosure are configured to provide FFR measurements over a length of a vessel of interest in a small, compact device that integrates with existing proximal and distal pressure measurement systems and does not require a separate power source.

29 Claims, 10 Drawing Sheets

(51) Int. Cl.
  *A61B 5/00* (2006.01)
  *A61B 5/026* (2006.01)
(52) U.S. Cl.
  CPC .......... *A61B 5/6851* (2013.01); *A61B 5/6852* (2013.01); *A61B 5/742* (2013.01); *A61B 5/026* (2013.01); *A61B 5/743* (2013.01); *A61B 2562/0247* (2013.01)
(58) Field of Classification Search
  CPC . A61B 5/743; A61B 5/021; A61B 2562/0247; A61B 5/02
  See application file for complete search history.

(56) References Cited

U.S. PATENT DOCUMENTS

| | | | |
|---|---|---|---|
| 5,549,113 A * | 8/1996 | Halleck | G08B 21/0453 600/484 |
| 5,568,815 A | 10/1996 | Raynes | |
| 5,715,827 A | 2/1998 | Corl | |
| 6,471,656 B1 * | 10/2002 | Shalman | A61B 5/0215 600/486 |
| 6,585,660 B2 | 7/2003 | Dorando | |
| 6,755,024 B1 | 6/2004 | Mao | |
| 7,335,161 B2 | 2/2008 | Von Arx et al. | |
| 8,753,274 B2 | 6/2014 | Ziv | |
| 8,836,514 B2 | 9/2014 | Rantala | |
| 9,301,699 B2 | 4/2016 | Hubinette | |
| 9,339,348 B2 | 5/2016 | Davies | |
| 2001/0021801 A1 | 9/2001 | Bardy | |
| 2001/0029337 A1 | 10/2001 | Pantages | |
| 2002/0062086 A1 * | 5/2002 | Miele | A61B 5/02028 600/483 |
| 2002/0151808 A1 | 10/2002 | Schwartzman | |
| 2002/0173724 A1 | 11/2002 | Dorando | |
| 2003/0093503 A1 | 5/2003 | Yamaki | |
| 2003/0100839 A1 | 5/2003 | Cohen | |
| 2003/0191400 A1 * | 10/2003 | Shalman | A61B 5/0215 600/486 |
| 2003/0216621 A1 | 11/2003 | Alpert | |
| 2004/0073132 A1 | 4/2004 | Maahs et al. | |
| 2004/0111045 A1 | 6/2004 | Sullivan | |
| 2004/0117204 A1 | 6/2004 | Mazar | |
| 2004/0133089 A1 * | 7/2004 | Kilcoyne | A61B 1/00147 600/350 |
| 2004/0138575 A1 | 7/2004 | Ueyama | |
| 2005/0015009 A1 | 1/2005 | Mourad | |
| 2006/0122542 A1 | 6/2006 | Smith | |
| 2006/0241505 A1 | 10/2006 | Ahmed | |
| 2007/0000498 A1 | 1/2007 | Glynn et al. | |
| 2007/0049845 A1 | 3/2007 | Fleischman | |
| 2007/0112274 A1 | 5/2007 | Heitzmann | |
| 2007/0179356 A1 | 8/2007 | Wessel | |
| 2008/0033255 A1 | 2/2008 | Essenpreis | |
| 2008/0046288 A1 | 2/2008 | Menon | |
| 2008/0234594 A1 | 9/2008 | Brooks | |
| 2009/0005703 A1 * | 1/2009 | Fasciano | A61B 5/031 600/561 |
| 2010/0107918 A1 | 5/2010 | Hess | |
| 2010/0210920 A1 * | 8/2010 | Ziv | A61B 5/0002 600/301 |
| 2010/0241013 A1 | 9/2010 | Hatib | |
| 2011/0071407 A1 * | 3/2011 | Hubinette | A61B 5/0002 600/485 |
| 2011/0085977 A1 | 4/2011 | Rosenmeier | |
| 2012/0139720 A1 | 6/2012 | Mazar | |
| 2012/0191467 A1 * | 7/2012 | LaPlante | G06Q 50/22 705/2 |
| 2012/0278008 A1 | 11/2012 | Davies | |
| 2013/0046190 A1 | 2/2013 | Davies | |
| 2013/0190633 A1 * | 7/2013 | Dorando | A61B 5/02158 600/486 |
| 2013/0285812 A1 | 10/2013 | Rantala | |
| 2013/0303871 A1 | 11/2013 | Brest | |
| 2013/0345574 A1 * | 12/2013 | Davies | A61B 5/02007 600/486 |
| 2014/0024956 A1 | 1/2014 | Purdy | |
| 2014/0135633 A1 | 5/2014 | Anderson | |
| 2014/0180140 A1 * | 6/2014 | Alpert | A61B 5/0004 600/486 |
| 2014/0207008 A1 | 7/2014 | Davies | |
| 2015/0080749 A1 | 3/2015 | Anderson | |
| 2016/0206214 A1 | 7/2016 | Davies | |

FOREIGN PATENT DOCUMENTS

| | | |
|---|---|---|
| JP | 2004358126 A | 12/2004 |
| JP | 2007289542 A | 11/2007 |
| JP | 2011050546 A | 3/2011 |
| WO | 0053081 A1 | 9/2000 |
| WO | 2000053081 A1 | 9/2000 |
| WO | 2001013779 A2 | 3/2001 |
| WO | WO 2001/013779 * | 3/2001 |
| WO | WO 2010-030882 A1 | 3/2010 |
| WO | 2010107918 A2 | 9/2010 |
| WO | 2011018468 A1 | 2/2011 |
| WO | WO 2011-034938 A2 | 3/2011 |
| WO | 2012093260 A1 | 7/2012 |
| WO | 2012093266 A1 | 7/2012 |

OTHER PUBLICATIONS

"Monitor." Oxford English Dictionary. Retrieved Feb. 6, 2018.
European Supplementary Search Report EP13738924.3, dated Nov. 6, 2015.
European Supplementary Search Report, 13864599.9, dated Jul. 1, 2016.
International Search Report and Written Opinion PCT/US2013/022041, dated May 5, 2012.
International Search Report and Written Opinion PCT /US2013/075433, dated Apr. 23, 2014.

* cited by examiner

INTERFACE DEVICES, SYSTEMS, AND METHODS FOR USE WITH INTRAVASCULAR PRESSURE MONITORING DEVICES

CROSS-REFERENCE TO RELATED APPLICATIONS

The present application claims priority to and the benefit of U.S. Provisional Patent Application No. 61/790,755, filed Mar. 15, 2013, which is hereby incorporated by reference in its entirety.

TECHNICAL FIELD

The present disclosure relates generally to the assessment of vessels and, in particular, the assessment of the severity of a blockage or other restriction to the flow of fluid through a vessel. Aspects of the present disclosure are particularly suited for evaluation of biological vessels in some instances. For example, some particular embodiments of the present disclosure are specifically configured for the evaluation of a stenosis of a human blood vessel.

BACKGROUND

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include angioplasty and stenting.

Coronary blood flow is unique in that it is affected not only by fluctuations in the pressure arising proximally (as in the aorta) but is also simultaneously affected by fluctuations arising distally in the microcirculation. Accordingly, it is not possible to accurately assess the severity of a coronary stenosis by simply measuring the fall in mean or peak pressure across the stenosis because the distal coronary pressure is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These potent vasodilator agents reduce the dramatic fluctuation in resistance (predominantly by reducing the microcirculation resistance associated with the systolic portion of the heart cycle) to obtain a relatively stable and minimal resistance value.

However, the administration of hyperemic agents is not always possible or advisable. First, the clinical effort of administering hyperemic agents can be significant. In some countries (particularly the United States), hyperemic agents such as adenosine are expensive, and time consuming to obtain when delivered intravenously (IV). In that regard, IV-delivered adenosine is generally mixed on a case-by-case basis in the hospital pharmacy. It can take a significant amount of time and effort to get the adenosine prepared and delivered to the operating area. These logistic hurdles can impact a physician's decision to use FFR. Second, some patients have contraindications to the use of hyperemic agents such as asthma, severe COPD, hypotension, bradycardia, low cardiac ejection fraction, recent myocardial infarction, and/or other factors that prevent the administration of hyperemic agents. Third, many patients find the administration of hyperemic agents to be uncomfortable, which is only compounded by the fact that the hyperemic agent may need to be applied multiple times during the course of a procedure to obtain FFR measurements. Fourth, the administration of a hyperemic agent may also require central venous access (e.g., a central venous sheath) that might otherwise be avoided. Finally, not all patients respond as expected to hyperemic agents and, in some instances, it is difficult to identify these patients before administration of the hyperemic agent.

To obtain FFR measurements, one or more ultra-miniature sensors placed on the distal portion of a flexible device, such as a catheter or guide wire used for catheterization procedures, are utilized to obtain the distal pressure measurement, while a sensor connected to a measurement instrument, often called the hemodynamic system, is utilized to obtain the proximal or aortic pressure measurement. Currently only large expensive systems or a combination of multiple devices connected to the distal pressure wire and the hemodynamic system can calculate and display an FFR measurement. In that regard, to calculate the FFR these devices require both the aortic or proximal pressure measurement and the coronary artery or distal pressure measurement. Accordingly, these systems require the catheter lab's hemodynamic system to have a high level analog voltage output. "High level" in this context generally implies 100 mmHg/Volt output. Unfortunately, there are many hemodynamic systems that don't provide a high level output. As a result, when using these hemodynamic systems, providing an FFR measurement is difficult if not impossible. Further, space in a typical catheter lab is extremely limited. Consequently, devices that are large and located in the catheter lab are disfavored compared to smaller derives, especially if the smaller device can provide much if not all of the functionality of the larger device. As a result, it is highly desirable to have a device that that can display FFR and yet is small and lightweight that can sit on, or near, the patient bed and be easily read by the physician.

Further, most pressure measurement devices require an extra source of power like an AC adapter or wall plug. This adds to wire clutter and available medical grade AC outlets are not often available near the patient bed. In addition, any device that uses AC power must undergo stringent safety precautions to reduce patient risk due to leakage currents. Batteries are another alternative for power. But, batteries must be replaced, disposed of correctly and have a finite shelf life.

Further still, FFR measurements are traditionally made with the proximal and distal pressure sensing devices maintained at static locations (e.g., within the aorta and distal of a suspected stenosis, in some instances) when the hyperemic agent is applied. Accordingly, the resulting FFR measurements provide data in the context of those static positions.

Accordingly, there remains a need for improved devices, systems, and methods for assessing the severity of a blockage in a vessel and, in particular, a stenosis in a blood vessel. In that regard, there remains a need for improved devices, systems, and methods for providing FFR measurements that have a small, compact size (e.g., suitable for hand-held use), integrate with existing proximal and distal pressure measurement devices, and provide FFR measurements over a length of a vessel of interest rather than at a single, static location.

SUMMARY

Embodiments of the present disclosure are configured to assess the severity of a blockage in a vessel and, in particular, a stenosis in a blood vessel. In some particular embodiments, the devices, systems, and methods of the present disclosure are configured to provide FFR measurements in a small, compact device that integrates with existing proximal and distal pressure measurement systems and provide FFR measurements over a length of a vessel of interest rather than at a single point.

In one embodiment, an interface for intravascular pressure sensing devices is provided. The interface comprises: a distal input configured to receive a distal pressure signal from a distal pressure sensing device; a proximal input configured to receive a proximal pressure signal from a proximal pressure sensing device; a pullback device configured to interface with a proximal portion of the distal pressure sensing device to cause translation of the distal pressure sensing device relative to the proximal pressure sensing device; a processor coupled to the distal input, proximal input, and the pullback device, the processor configured to calculate a pressure differential between the distal pressure and the proximal pressure based on the received distal pressure signal and the received proximal pressure signal obtained as the pullback device translates the distal pressure sensing device relative to the proximal pressure sensing device; and a display in communication with the processor and configured to display the pressure differential calculated by the processor including a relative position of the distal pressure sensing device to the proximal pressure sensing device associated with the calculated pressure differential. In some embodiments, the distal input, distal output, proximal input, proximal output, and processor are secured to a housing. Further, in some instances the distal pressure sensing device is a pressure-sensing guide wire and the proximal pressure sensing device is a pressure-sensing catheter configured for use with the hemodynamic system.

In another embodiment, a system for evaluating a vascular stenosis is provided. The system comprises: a distal pressure sensing device sized and shaped for insertion into human vasculature; a proximal pressure sensing device sized and shaped for insertion into human vasculature; and an interface, where the interface includes: a distal input configured to receive a distal pressure signal from a distal pressure sensing device; a proximal input configured to receive a proximal pressure signal from a proximal pressure sensing device; a pullback device configured to interface with a proximal portion of the distal pressure sensing device to cause translation of the distal pressure sensing device relative to the proximal pressure sensing device; a processor coupled to the distal input, proximal input, and the pullback device, the processor configured to calculate a pressure differential between the distal pressure and the proximal pressure based on the received distal pressure signal and the received proximal pressure signal obtained as the pullback device translates the distal pressure sensing device relative to the proximal pressure sensing device; and a display in communication with the processor and configured to display the pressure differential calculated by the processor including a relative position of the distal pressure sensing device to the proximal pressure sensing device associated with the calculated pressure differential.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
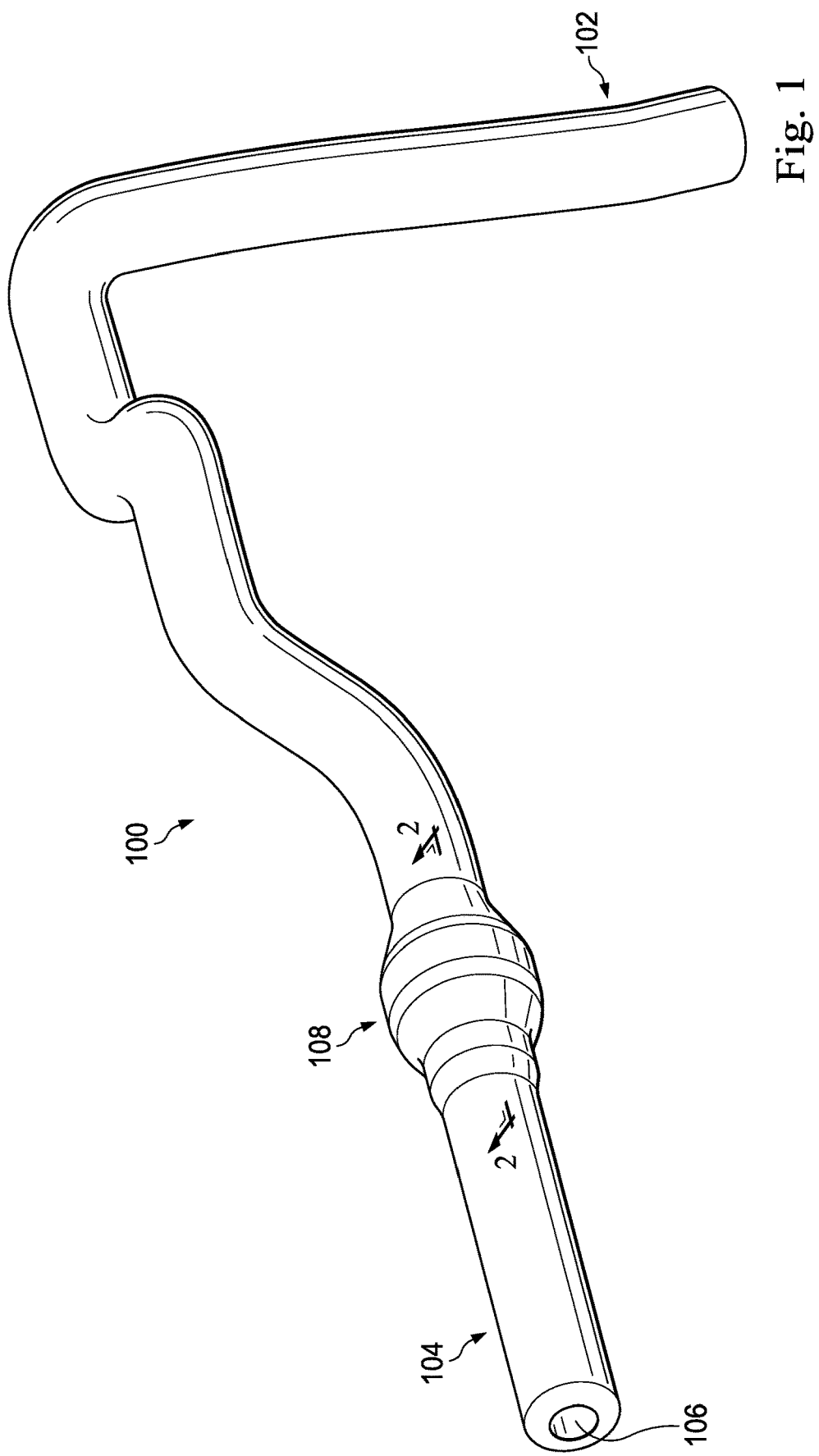
FIG. 1 is a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 2:
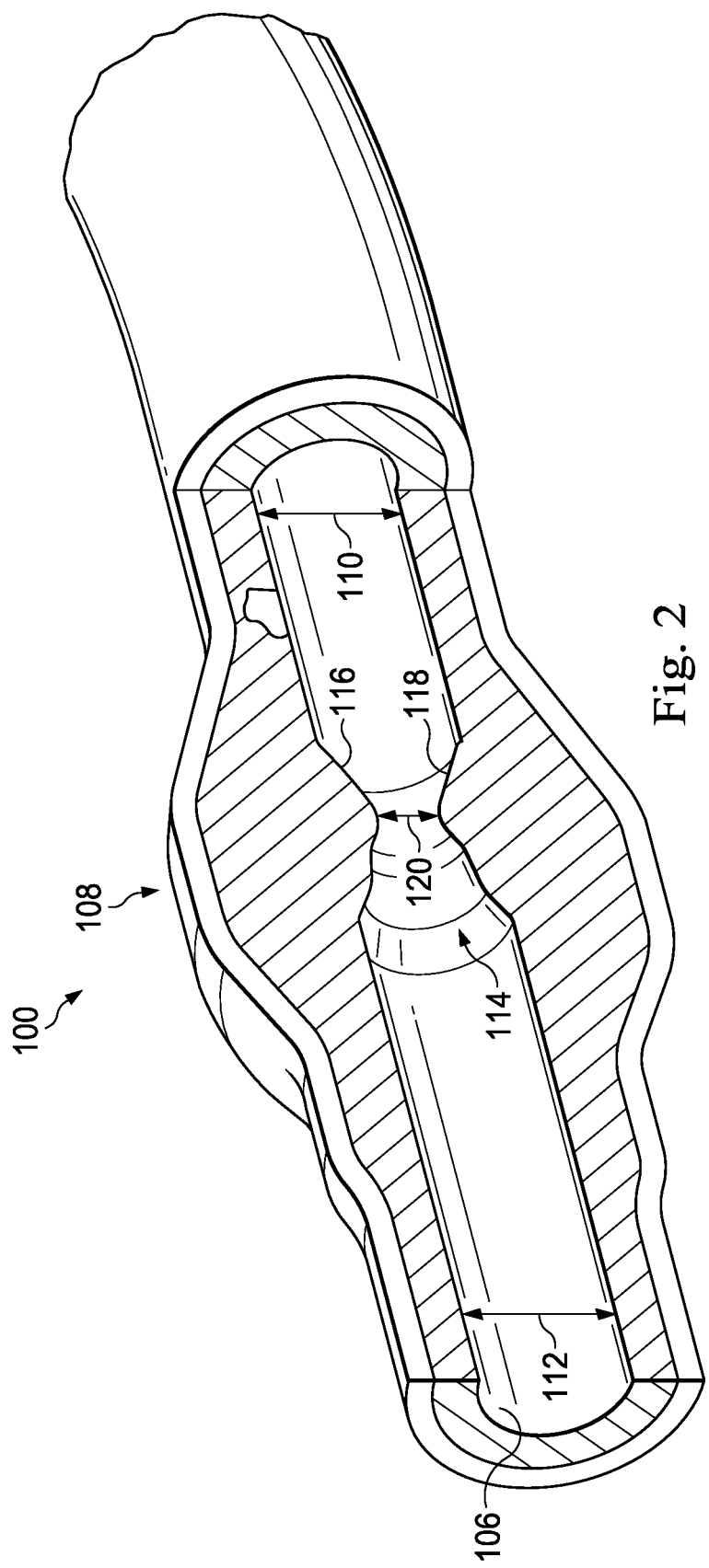
FIG. 2 is a diagrammatic, partial cross-sectional perspective view of a portion of the vessel of FIG. 1 taken along section line 2-2 of FIG. 1.
Figure 3:
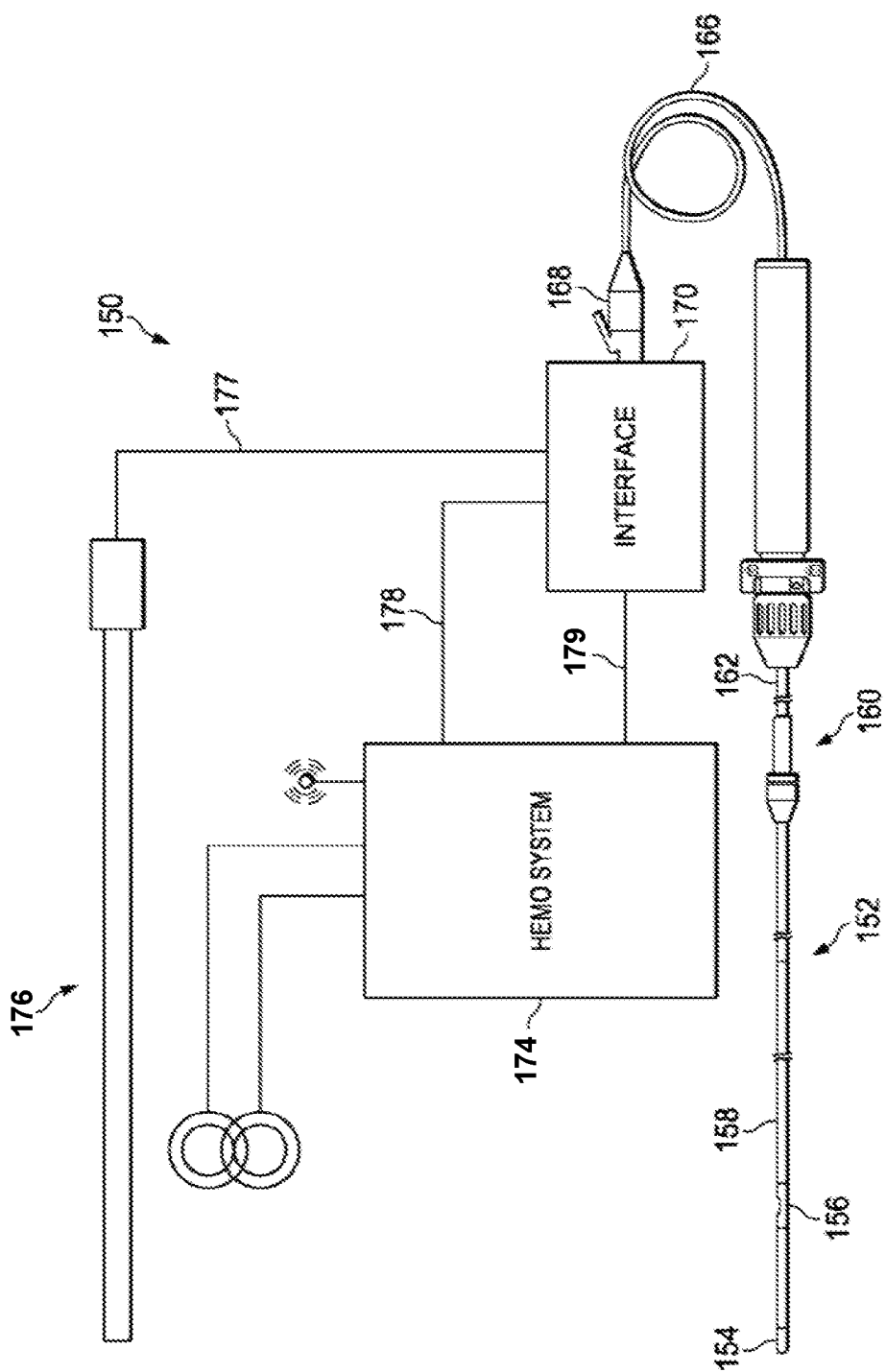
FIG. 3 is a diagrammatic, partial cross-sectional perspective view of the vessel of FIGS. 1 and 2 with instruments positioned therein according to an embodiment of the present disclosure.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

The vessel 100 can include instruments 152 and 176 positioned therein according to an embodiment of the present disclosure. In general, instruments 152 and 176 may be any form of device, instrument, or probe sized and shaped to be positioned within a vessel. In the illustrated embodiment, instrument 152 is generally representative of a guide wire, while instrument 176 is generally representative of a catheter. In that regard, instrument 152 extends through a central lumen of instrument 176. However, in other embodiments, the instruments 152 and 176 take other forms. In that regard, the instruments 152 and 176 are of similar form in some embodiments. For example, in some instances, both instruments 152 and 176 are guide wires. In other instances, both instruments 152 and 176 are catheters. On the other hand, the instruments 152 and 176 are of different form in some embodiments, such as the illustrated embodiment, where one of the instruments is a catheter and the other is a guide wire. Further, in Some instances, the instruments 152 and 176 are disposed coaxial with one another. In other instances, one of the instruments extends through an off-center lumen of the other instrument. In yet other instances, the instruments 152 and 176 extend side-by-side. In some particular embodiments, at least one of the instruments is as a rapid-exchange device, such as a rapid-exchange catheter. In such embodiments, the other instrument is a buddy wire or other device configured to facilitate the intro duction and removal of the rapid-exchange device. Further still, in other instances, instead of two separate instruments 152 and 176 a single instrument is utilized. In that regard, the single instrument incorporates aspects of the functionalities (e.g., data acquisition) of both instruments 152 and 176 in some embodiments.

Instrument 152 is configured to obtain diagnostic information about the vessel 100. In that regard, the instrument 152 includes one or more sensors, transducers, and/or other monitoring elements configured to obtain the diagnostic information about the vessel. The diagnostic information includes one or more of pressure, flow (velocity), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 152 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 152 in some instances. In some instances, at least one of the one or more sensors, transducers, and/or other monitoring elements is positioned at the distal tip of the instrument 152.

The instrument 152 includes at least one element configured to monitor pressure within the vessel 100. The pressure monitoring element can take the form of a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 152 is sized such that it can be positioned through the stenosis 108 without significantly impacting fluid flow across the stenosis, which would impact the distal pressure reading. Accordingly, in some instances the instrument 152 has an outer diameter of 0.018" or less. In some embodiments, the instrument 152 has an outer diameter of 0.014" or less.

Instrument 176 is also configured to obtain diagnostic information about the vessel 100. In some instances, instrument 176 is configured to obtain the same diagnostic information as instrument 152. In other instances, instrument 176 is configured to obtain different diagnostic information than instrument 152, which may include additional diagnostic information, less diagnostic information, and/or alternative diagnostic information. The diagnostic information obtained by instrument 176 includes one or more of pressure, flow (velocity), images (including images obtained using ultrasound (e.g., IVUS), OCT, thermal, and/or other imaging techniques), temperature, and/or combinations thereof. Instrument 176 includes one or more sensors, transducers, and/or other monitoring elements configured to obtain this diagnostic information. In that regard, the one or more sensors, transducers, and/or other monitoring elements are positioned adjacent a distal portion of the instrument 176 in some instances. In that regard, the one or more sensors, transducers, and/or other monitoring elements are positioned less than 30 cm, less than 10 cm, less than 5 cm, less than 3 cm, less than 2 cm, and/or less than 1 cm from the instrument 176 in some instances. In some instances, at least one of the one or more sensors, transducers, and/or other monitoring elements is positioned at the distal tip of the instrument 132.

Similar to instrument 152, instrument 176 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM Sensis, Mennen Horizon XVu, and Philips Xper IM Physiomonitoring 5 and that include pressure monitoring elements can be utilized for instrument 176 in some instances.

In accordance with aspects of the present disclosure, at least one of the instruments 152 and 176 is configured to monitor a pressure within the vessel 100 distal of the stenosis 108 and at least one of the instruments 152 and 176 is configured to monitor a pressure within the vessel proximal of the stenosis. In that regard, the instruments 130, 176 are sized and shaped to allow positioning of the at least one element configured to monitor pressure within the vessel 100 to be positioned proximal and/or distal of the stenosis 108 as necessary based on the configuration of the devices. A position suitable for measuring pressure distal of the stenosis 108 is less than 5 cm, less than 3 cm, less than 2 cm, less than 1 cm, less than 5 mm, and/or less than 2.5 mm from the distal end of the stenosis 108 (as shown in FIG. 2) in some instances. A position that is suitable for monitoring the pressure proximal of the stenosis in some instances is positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery. In some instances, the proximal pressure measurement is referred to as the aortic pressure.

As will be discussed below, in some implementations instrument 152 is moved through the vessel 100 while obtaining pressure measurements. In that regard, in some implementations the instrument 152 is initially positioned distal of a region of interest and then pull backed through and across the region of interest. To facilitate movement of the instrument 152 through the vessel, a proximal section of the instrument is coupled to a pullback device and/or other actuator configured to impart translational movement to the instrument 152 and, in particular, the at least one element of the instrument configured to monitor pressure within the vessel 100. In some implementations, the pullback device is configured to move at least a portion of the instrument 152 at a continuous speed for a fixed distance (e.g., 5 cm, 10 cm, 15 cm, or otherwise) and/or time (e.g., 10 seconds, 20 seconds, 30 seconds, 40 seconds, 50 seconds, 60 seconds, or otherwise). In other implementations, the pullback device is configured to move at least a portion of the instrument 152 in a step-wise manner (i.e., move for a certain distance/time and then stop for a certain amount of time). In some instances, the timing of the step-wise movement is coordinated with the patient's heartbeat. In that regard, as discussed below some implementations of the present disclosure rely on diagnostic windows corresponding to only a portion of the patients heartbeat cycle. Accordingly, in some instances it is desirable to maintain the instrument 152 in a fixed position for one or more heartbeat cycles before moving the instrument 152 to a next position. However, in other instances the instrument 152 is moved continuously through the vessel, while still using only a portion of the patient's heartbeat cycle for the diagnostic window. In some instances, the pullback device includes some features similar to one or more of the pullback devices disclosed in U.S. patent application Ser. No. 11/250,159, filed Oct. 12, 2005, which is hereby incorporated by reference in its entirety, the R100 Pullback Device available from Volcano Corporation, the Trak Back® II Device available from Volcano Corporation, and/or the SpinVision® Pullback Device available from Volcano Corporation. To that end, generally the instrument 152 will not require rotation and, therefore, the components of such pullback devices configured to impart rotation on the received instrument (or a part thereof) are omitted and/or disabled in some implementations.

Figure 4:
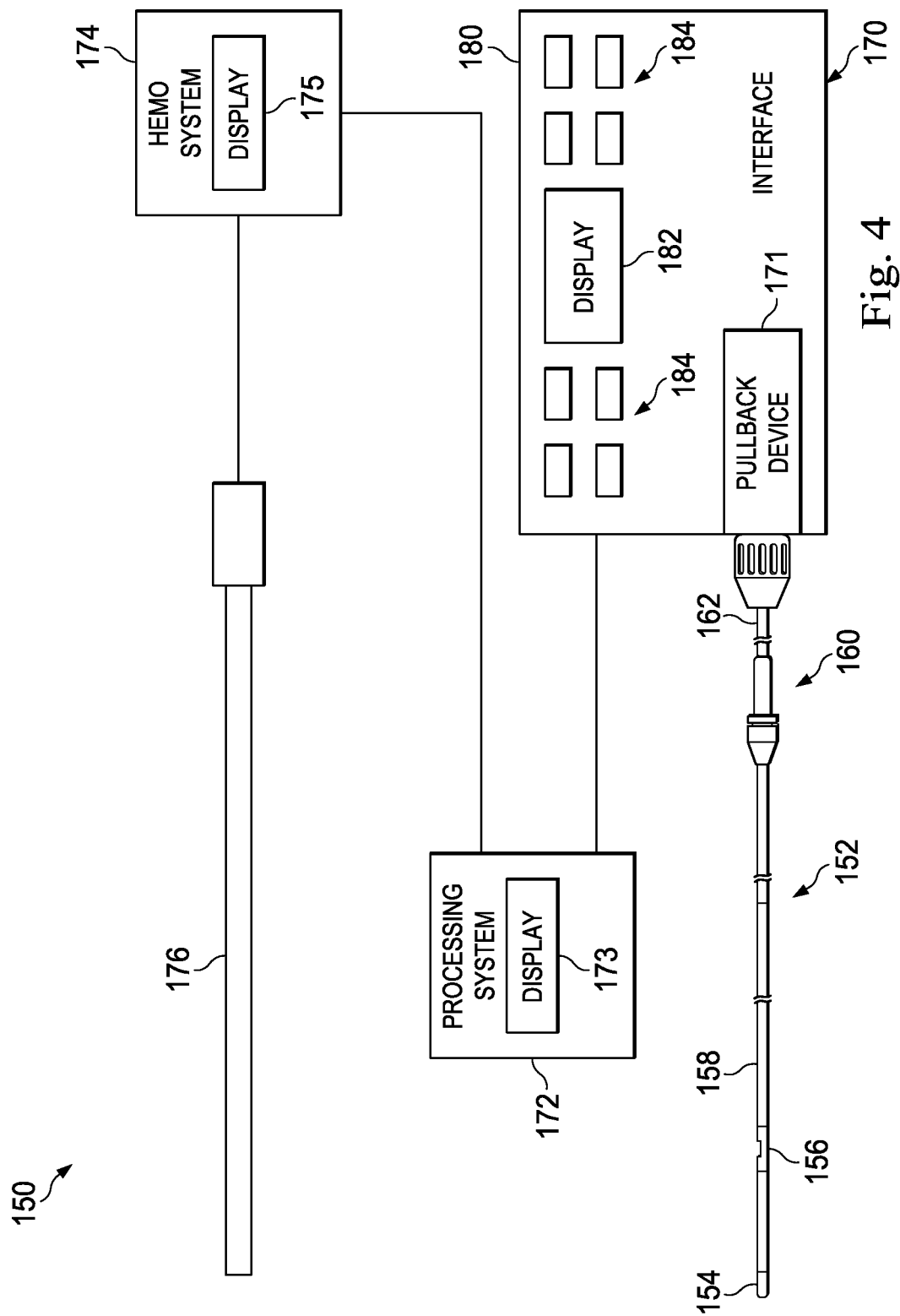
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 152 and 176 discussed above. Accordingly, in some instances the instrument 152 includes features similar to those discussed above with respect to instruments 152 and 176 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 152 is positioned over and coupled to a proximal portion of the shaft 158. A proximal end portion 162 of the instrument 152 is coupled to an interface 170. In particular, in some instances the proximal end portion 162 is coupled to a pullback device 171 of the interface 170. The pullback device 171 is incorporated into a housing of the interface 170 in some instances. In other instances, the pullback device 171 is in a separate housing from the interface 170, but in communication with one or more electronic components of the interface 170. Interface 170 is a patient interface module (PIM) in some instances. In some instances, the pullback device 171 and/or adjacent component of the interface 170 include electrical connectors to facilitate communication of data and/or signals between the instrument 152 and the interface 170. In some instances, the instrument 152 communicates data and/or signals wirelessly with one or more components of the interface 170. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a processing system 172 having a display 173. Accordingly, the interface 170 and any intervening connections facilitate communication between the one or more sensors, transducers, and/or other monitoring elements of the instrument 152 and the processing system 172. In that regard, it is understood that any communication pathway (e.g., connection 166) between the instrument 152 and the interface 170 may be utilized, including physical connections (including electrical, optical, and/or fluid connections), wireless connections, and/or combinations thereof. Similarly, it is understood that any communication pathway (e.g., connections 178 and 179) between the interface 170 and the processing system 172 may be utilized, including physical connections (including electrical, optical, and/or fluid connections), wireless connections, and/or combinations thereof. Accordingly, it is understood that additional components (e.g., connectors, antennas, routers, switches, etc.) not illustrated in FIG. 4 may be included to facilitate communication between the instrument 152, the interface 170, and the processing system 172 (e.g., connector 168).

The system 150 also includes an instrument 176. In that regard, in some instances instrument 176 is suitable for use as at least one of instruments 152 and 176 discussed above. Accordingly, in some instances the instrument 176 includes features similar to those discussed above with respect to instruments 152 and 132. In the illustrated embodiment, the instrument 176 is a catheter-type device. In that regard, the instrument 176 includes one or more sensors, transducers, and/or other monitoring elements adjacent a distal portion of the instrument configured to obtain the diagnostic information about the vessel. In the illustrated embodiment, the instrument 176 includes a pressure sensor configured to monitor a pressure within a lumen in which the instrument 176 is positioned. In one particular embodiment, instrument 176 is a pressure-sensing catheter that includes a fluid column extending along its length. In such an embodiment, a hemostasis valve is fluidly coupled to the fluid column of the catheter, a manifold is fluidly coupled to the hemostasis valve, and tubing extends between the components as necessary to fluidly couple the components. In that regard, the fluid column of the catheter is in fluid communication with a pressure sensor via the valve, manifold, and tubing. In some instances, the pressure sensor is part of or in communication with a hemo system 174 having a display 175. In other instances, the pressure sensor is a separate component positioned between the instrument 176 and the hemo system 174. In some instances, the hemo system 174 includes features similar to those found in Siemens AXIOM Sensis, Mennen Horizon XVu, and Philips Xper IM Physiomonitoring 5.

As shown, the hemo system 174 is in communication with the processing system 172 to facilitate the transfer of data and/or signals between the systems. In particular, in some implementations data obtained by instrument 152 is passed from processing system 172 to hemo system 174, while data obtained by instrument 176 is passed from hemo system 174 to processing system 172. To that end, in implementations where instrument 152 is utilized to obtain pressure measurements at a point of interest or across a region of interest within a vessel and instrument 176 is utilized to obtain a reference pressure measurement (e.g., an aortic pressure measurement, in some instances), the combined data from the instruments 152 and 176 can be utilized to calculate FFR and/or similar pressure ratio calculation. For example, in some instances FFR or similar pressure ratio calculation is determined for pressure measurements obtained during a pullback of the instrument 152 using pullback device 171. In this manner, the resulting FFR or similar pressure ratio calculation provides an indication of severity of a stenosis or lesion along the length of the vessel that the instrument 152 has been moved through during the pullback. Such information can be utilized to determine an appropriate treatment plan, including the determination of the type(s) of treatment(s) to be applied and where such treatment(s) should be utilized.

In some embodiments, the connection(s) between the instrument 152, the interface 170, the processing system 172, and the hemo system 174 includes a wireless connection. In some instances, the connection(s) includes a communication link over a network (e.g., intranet, internet, telecommunications network, and/or other network). In that regard, it is understood that the processing system 172 and/or hemo system 174 is positioned remote from an operating area where the instrument 152 is being used in some instances. Having the connection(s) include a connection over a network can facilitate communication between the instrument 152 and the remote processing system 172 and/or remote hemo system 174 regardless of whether the computing device is in an adjacent room, an adjacent building, or in a different state/country. Further, it is understood that the communication pathway(s) is a secure connection in some instances. Further still, it is understood that, in some instances, the data communicated over one or more portions of the communication pathway(s) is encrypted.

It is understood that one or more components of the system 150 are not included, are implemented in a different arrangement/order, and/or are replaced with an alternative device/mechanism in other embodiments of the present disclosure. Alternatively, additional components and/or devices may be implemented into the system. Generally speaking, the communication pathway between either or both of the instruments 152, 176 and the computing device 172 may have no intermediate nodes (i.e., a direct connection), one intermediate node between the instrument and the computing device, or a plurality of intermediate nodes between the instrument and the computing device.

In some embodiments, the interface 170 includes a processor and random access memory and is programmed to execute steps associated with the data acquisition and analysis described herein. For example, in some embodiments the interface 170 is configured to receive and display pressure readings from one or both of the instruments 152 and 176 and/or calculate (and display) FFR or other pressure ratio based on the pressure measurements obtained from the instruments 152 and 176. Accordingly, in some instances the data obtained by instrument 176 is passed through hemo system 174 and processing system 172 to interface 170. However, as discussed below with respect to FIGS. 5 and 6, other systems of the present disclosure allow the interface 170 to obtain the data from instrument 176 more directly (e.g., connection 177). It is understood that any steps related to data acquisition, data processing, instrument control, and/or other processing or control aspects of the present disclosure, including those incorporated by reference, may be implemented by the interface 170 using corresponding instructions stored on or in a non-transitory computer readable medium accessible by the computing device. In some embodiments, the interface 170 includes one or more processing and/or signal conditioning features and/or associated components/circuitry as described in U.S. Pat. No. 6,585,660, which is hereby incorporated by reference in its entirety.

In the illustrated embodiment of FIG. 4, the interface 170 includes a housing 180. The housing 180 contains the electronic components of the interface 170. Exemplary embodiments of electronic component arrangements suitable for interface 170 are described below with respect to FIGS. 7-9. In some embodiments, the interface 170 is sized to be handheld and/or sized to be positioned on or near a patient bed (e.g., attached to a bed rail or IV pole). In that regard, in some instances the interface 170 is similar in size to the SmartMap® Pressure Instrument available from Volcano Corporation, which has housing dimensions of approximately 15.75 cm (6.3") wide, 8.853 cm (3.54") tall, and 4.48 cm (1.79") deep. Generally, the interface 170 has a width between about 5 cm and about 25 cm, a height between about 5 cm and about 25 cm, and a depth between about 1 cm and about 10 cm.

The interface 170 also includes a display 182 and buttons 184. In that regard, the display 182 is configured to display various diagnostic information such as distal pressure, proximal pressure, pressure differentials (including FFR), distal pressure waveforms, proximal pressure waveforms, and/or additional diagnostic parameters. In some embodiments, in order to conserve the amount of energy needed for operation of the interface 170, the display 182 is a low-power display, such as a liquid crystal display. However, any type of visual display may be utilized, including color and/or monochromatic displays. In some instances, the display 182 covers a majority of a front surface of the display. In that regard, in some particular embodiments the display 182 is a touchscreen. In such embodiments, the buttons 184 may be virtual buttons (i.e., displayed on the touchscreen display 182), physical buttons, and/or combinations thereof. Generally, the buttons 184 are configured to facilitate configuration and operation of the interface 170 and/or pullback device 171. It is understood that any number of buttons may be utilized and that buttons may be utilized for multiple functionalities and/or be dedicated to a single function. As a result, the interface 170 may include one or more virtual or physical buttons configured to facilitate use of the interface in the manners described herein. Further, in some instances, in addition to or in lieu of display 182 the interface 170 includes a video output configured to send video/display signals to a separate display device (e.g., display 173 of the processing system 172, display 175 of the hemo system 174, a standalone display, and/or a display integrated with another medical system).

Figure 5:
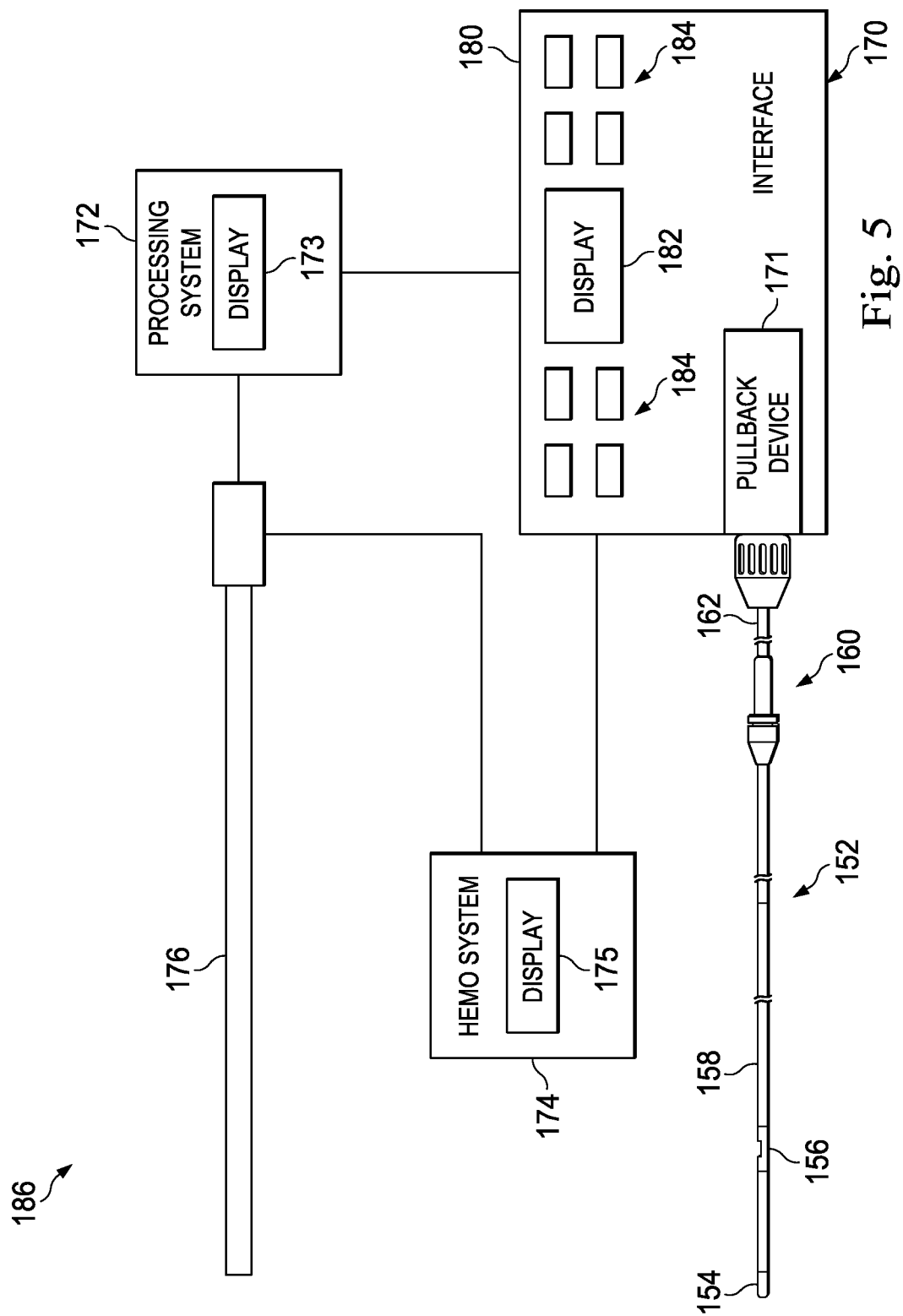
FIG. 5 is a diagrammatic, schematic view of a system according to an embodiment of the present disclosure.

Referring now to FIG. 5, shown therein is a system 186 according to another embodiment of the present disclosure. In that regard, FIG. 5 is a diagrammatic, schematic view of the system 186. The system 186 includes many components and features similar to system 150 described above. Accordingly, the following description will focus on the differences of system 186. As shown, the interface 170 of system 186 is communicates directly with hemo system 174, rather than needing to communicate through processing system 172. To that end, in some instances the interface 170 is configured to output pressure measurements obtained by instrument 152 to the hemo system 174. The interface 170 is also configured to output the pressure measurements obtained by instrument 152 to the processing system 172. Further, in some instances the interface 170 is configured to receive pressure measurements obtained by instrument 176 from the hemo system 174. In some instances, the interface utilizes the pressure measurements obtained by the instruments 152 and 176 to make FFR or other pressure ratio calculations, including during a pullback of instrument 152. Further, in some implementations the interface outputs the pressure measurements of instrument 176 received from hemo system 174 to the processing system 172.

Figure 6:
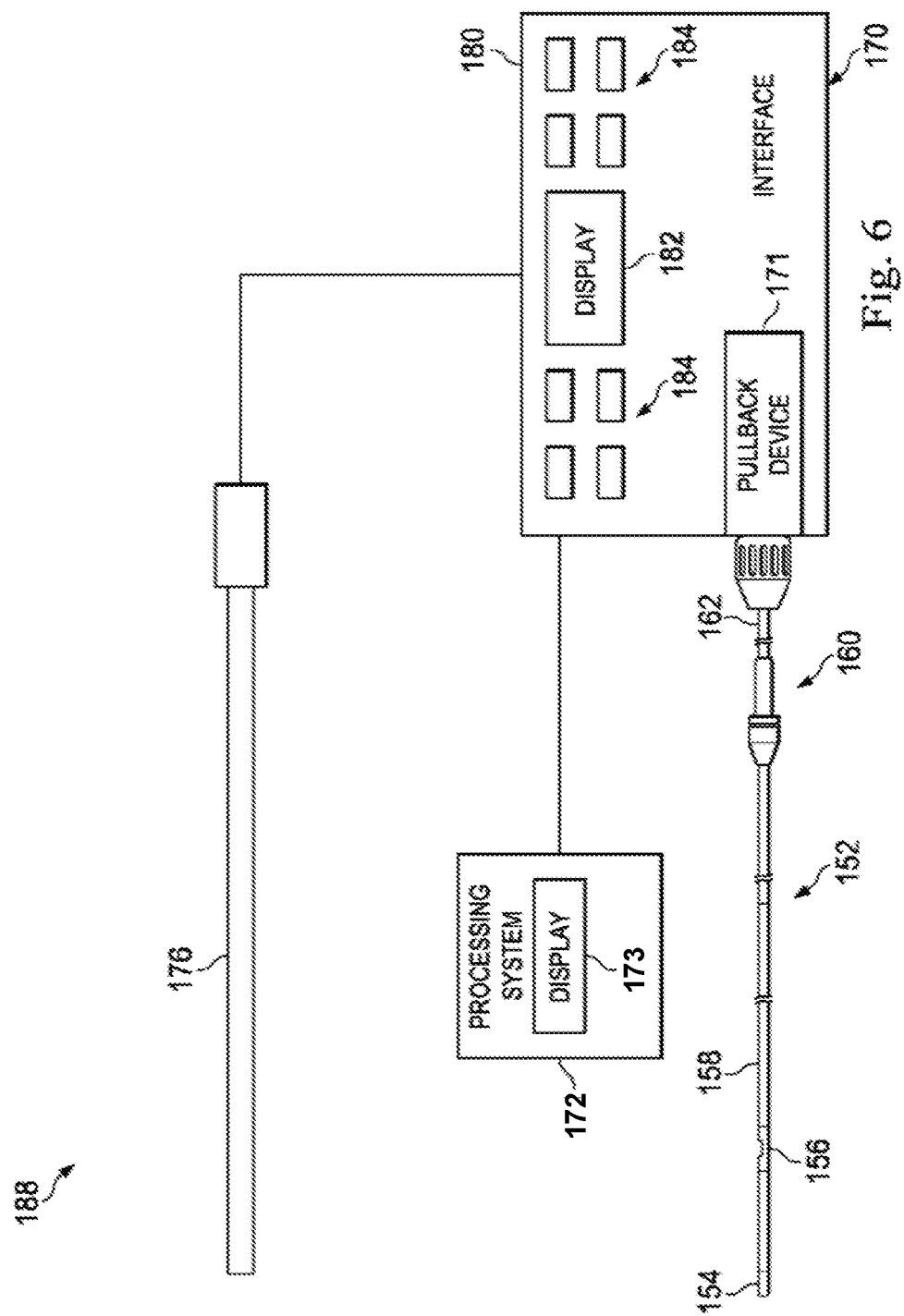
FIG. 6 is a diagrammatic, schematic view of a system according to an embodiment of the present disclosure.

Referring now to FIG. 6, shown therein is a system 188 according to another embodiment of the present disclosure. In that regard, FIG. 6 is a diagrammatic, schematic view of the system 188. The system 188 includes many components and features similar to systems 150 and 186 described above. Accordingly, the following description will focus on the differences of system 188. As shown, in the embodiment of FIG. 6 the interface 170 is configured to interface with both instruments 152 and 176. Accordingly, in some instances the interface 170 is configured to communicate data obtained by each of instruments 152 and 176 to the processing system 172, which is a hemo system in some implementations. To that end, in some instances the interface 170 includes different outputs to the processing system 172 for each of the instruments 152 and 176. In other instances, the data for both instruments 152 and 176 are sent over a common, shared output from interface 170. Exemplary implementations of the interface 170 in accordance with the schematic of system 188 are described below.

Figure 7:
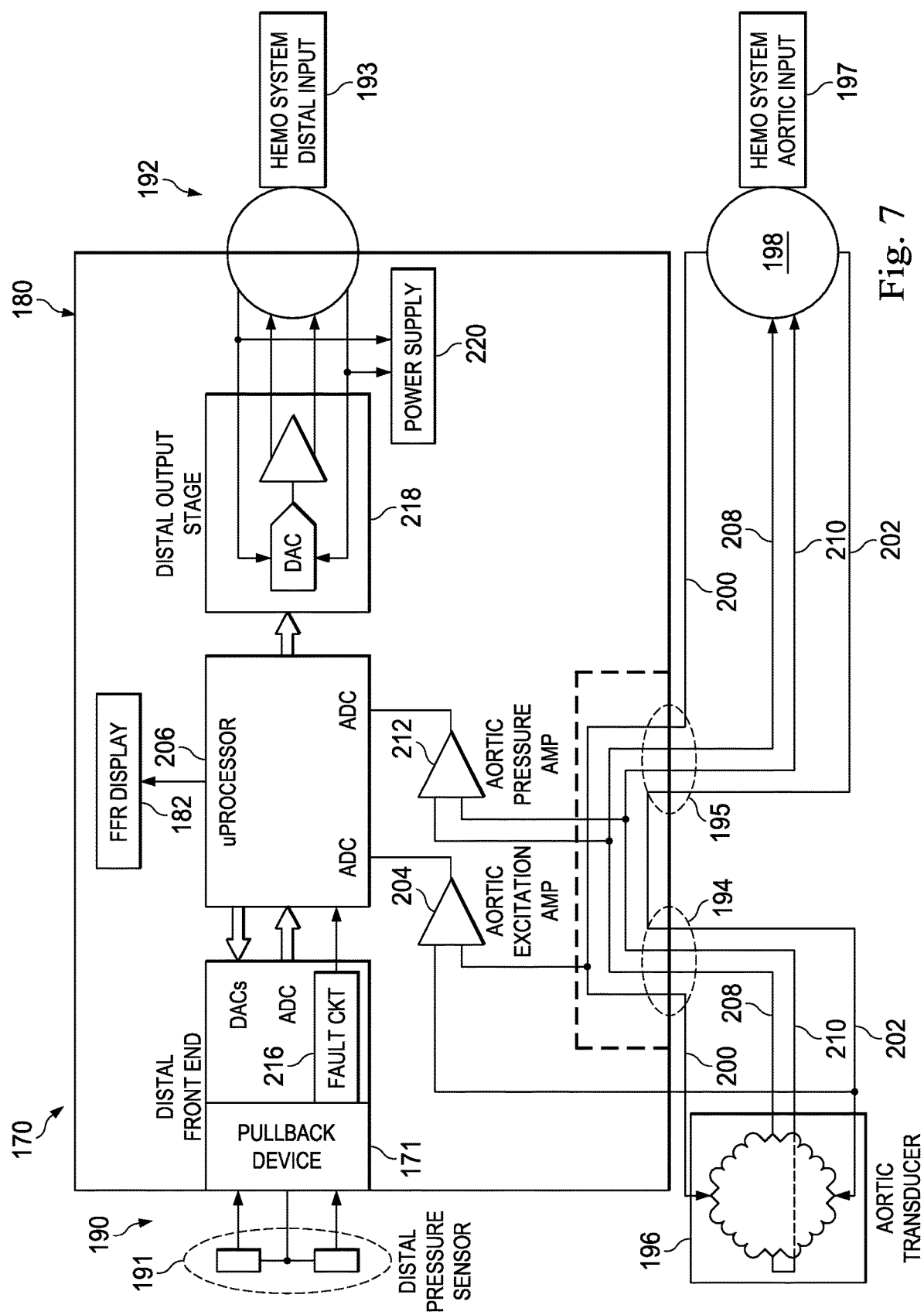
FIG. 7 is a diagrammatic, schematic view of an interface device of the system of FIG. 6 according to an embodiment of the present disclosure.

Referring now to FIG. 7, shown therein is a schematic of the interface 170 according to an exemplary embodiment of the present disclosure. In that regard, the interface 170 includes an input connector 190 associated with the pullback device 171 for receiving a proximal end of instrument 152. Accordingly, in some embodiments with an arrangement similar to that shown in FIG. 6, input connector 190 is configured to receive the proximal end of the instrument 152 and facilitate communication of signals to and from a distal pressure sensing component 191 of the instrument 152. The interface 170 also includes an output connector 192 configured to send a distal pressure signal to a distal pressure input 193 of a processing system 172, hemo system 174, or other computing device. Accordingly, in some embodiments with an arrangement similar to that shown in FIG. 6, output connector 192 is configured to send the distal pressure signal to an input of processing system 172. In that regard, in some embodiments processing system 172 is a hemo system and the distal pressure signal is modulated based on the hemo system's excitation voltage to provide a low level output of the distal pressure signal to the hemo system. A low level output in this context is typically 5 µV/Vexc/mmHg, where Vexc is the excitation voltage. However, larger or smaller level outputs are used in some instances.

In some embodiments, the output connector 192 is also used to facilitate energy harvesting from the processing system, hemo system, or other pressure measuring system. In that regard, to eliminate the need for an additional power supply within the interface 170, a power supply circuit 220 extracts a small amount of power from the system's excitation voltage associated with the distal pressure input 193. The power supply circuit 220 converts the extracted energy into the power needed to run the remaining circuitry of the interface 170. In some instances, the power supply circuit 220 is configured to be the only power source used to power the components of interface 170. Since the excitation signal can be AC, positive or negative DC, and/or have various wave form shapes and voltages, the power supply circuit 220 must be able to accept these and convert to a regulated power supply. In that regard, the voltage extracted from the excitation signal is converted to a regulated Vcc voltage to operate the low power circuitry using a buck or boost regulator depending on the input voltage. A current limiter minimizes distortion to the system's waveform at the peaks. In some instances, the current is limited to a level below the AAMI transducer limits as to be compatible with most hemo systems. In some instances, the system's excitation voltage meets the IEC 60601-2-34 standard. In some alternative embodiments, the power supply circuit is configured to interface with a battery or other rechargeable power supply device that can be utilized to power the components of the interface. In some alternative embodiments, the power supply circuit is configured to interface with an AC adapter that is to be plugged into a wall outlet in order to provide power to the components of the interface.

The interface 170 also includes input/output connectors 194 and 195 for interfacing with a proximal pressure measurement system. In some particular embodiments, the input/output connectors 194 and 195 are configured to work with a pressure monitoring device of a hemo stat system. Generally, the input/output connector 194 is configured to receive signals from a proximal pressure sensing component 196. Accordingly, in some embodiments with an arrangement similar to that shown in FIG. 6, input/output connector 194 is configured to receive signals from instrument 176, where the proximal pressure sensing component 196 is a pressure sensing component associated with the instrument 176. The input/output connector 195 is configured to send a proximal pressure signal to a proximal pressure input 197 of a processing system, hemo system, or other computing device. Accordingly, in some embodiments with an arrangement similar to that shown in FIG. 6, the input/output connector 195 is configured to send the proximal pressure signal to an input of computing device 172 over connection 178.

In the illustrated embodiment of FIG. 7, conductors 200 and 202 carry the excitation signal to the proximal pressure sensing component 196. An amplifier 204 is electrically connected to the conductors 200 and 202 as shown. The amplifier 204 is an operational amplifier in some embodiments. The excitation signal extracted by amplifier 204 is sent to a microprocessor 206. As will be discussed below, the excitation signal is utilized to evaluate the proximal pressure signals received from the proximal pressure sensing component 196.

In the illustrated embodiment of FIG. 7, conductors 208 and 210 carry the proximal pressure signal from the proximal pressure sensing component 196 back to the proximal pressure input 197 of the computing device. In that regard, an amplifier 212 is electrically connected to the conductors 208 and 210 as shown. The amplifier 212 is an operational amplifier in some embodiments. The amplifier 212 is configured to monitor or sample the proximal pressure signal being supplied from the proximal pressure sensing component 196. The sampled proximal pressure signal is then sent to the microprocessor 206. Accordingly, both the excitation signal/voltage sampled from conductors 200 and 202 and the proximal pressure signal sampled from conductors 208 and 210 are fed to the microprocessor 206. In some instances, the microprocessor 206 calculates the proximal pressure based on the excitation signal voltage (Vexc), and the proximal pressure sensing component's output. In that regard, the proximal pressure sensing component's output conforms to the AAMI standard of 5 uV/Vexc/mmHg in some instances. For an AC excitation signal, the microprocessor 206 must measure the proximal pressure signal voltage in synchrony with the excitation waveform. In some instances, rather than the low-level inputs described above, the proximal pressure signal is received by the interface 170 as a high level signal. For example, the proximal pressure signal is a high level signal from a Volcano LoMap (available from Volcano Corporation) or from an external hemo system.

In some embodiments, the input/output connectors 194 and 195 are also used to facilitate energy harvesting from the hemo system or other pressure measuring system. In that regard, to eliminate the need for an additional power supply within the interface 170, the power supply circuit 220 may be connected to conductors 200 and 202 and utilized to extract a small amount of power from the hemo system's excitation voltage for the proximal pressure sensing component 196 and convert it into the power needed to run the remaining circuitry of the interface 170. As noted above, when connected to the proximal pressure sensing side the power supply circuit 220 is still configured to extract power from the excitation signal sent from the controller/computing device such that the extracted power can be used to power the components of interface 170. Since the excitation signal can be AC, positive or negative DC, and/or have various wave form shapes and voltages, the power supply circuit 220 must be able to accept these and convert to a regulated power supply without distorting the waveform that continues on to the proximal pressure sensing component 196. This is necessary to avoid affecting the pressure measurements obtained by the proximal pressure sensing component 196. The voltage extracted from the excitation signal is converted to a regulated Vcc voltage to operate the low power circuitry using a buck or boost regulator depending on the input voltage.

Figure 8:
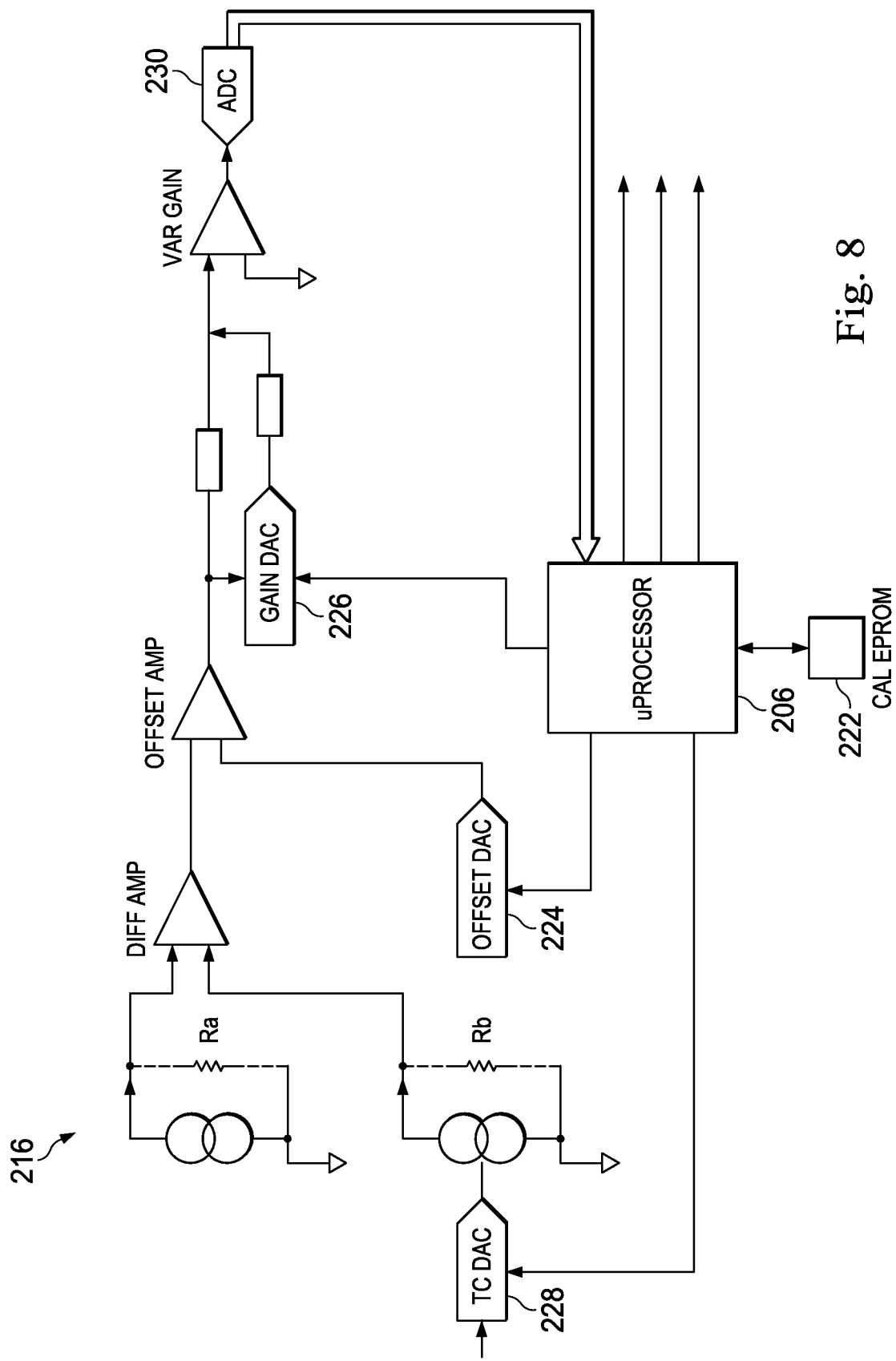
FIG. 8 is a diagrammatic, schematic view of a portion of the interface device of FIG. 7 according to an embodiment of the present disclosure.

As noted above, the interface 170 is also configured to receive and process distal pressure signals from a distal pressure sensing component 191 of instrument 152. In that regard, a signal conditioning portion 216 of the interface 170 is in communication with input 190 that receives the distal pressure signal. Referring now to FIG. 8, shown therein is a schematic of a portion the interface 170 according to an exemplary embodiment of the present disclosure. In particular, FIG. 8 shows a schematic of an exemplary embodiment of signal conditioning portion 216 of the interface 170. In that regard, the signal conditioning portion 216 is configured to condition signals received from the distal pressure measurement device. The signal conditioning portion 216 provides the excitation and amplification required for the distal pressure measurement device's pressure sensors, Ra and Rb, which collective form distal pressure sensing component 191 in some instances. In some implementations, the signal conditioning portion 216 is incorporated as part of the pullback device 171. In other implementations, the signal conditioning portion is adjacent to or spaced from the pullback device 171.

Calibration coefficients provided by the distal pressure measurement device utilizing an EPROM in the device connector, for example, are read to adjust the gain, offset, and temperature sensitivity for the device. The read values are used to adjust the three Digital to Analog Converters (DACs) 224, 226, and 228, in the distal pressure front end circuitry 216 that control the gain, offset, and temperature (TC) compensation, respectively. The distal pressure signal is then digitized with an Analog to Digital Converter 230, ADC, and sent to the microprocessor 206. The microprocessor 206 can then display the distal pressure, display a waveform of the distal pressure, or utilize the distal pressure or the distal pressure waveform for additional calculations. For example, in some instances the microprocessor utilizes the distal pressure and/or distal pressure waveform with the proximal pressure and/or proximal pressure waveform to calculate FFR, calculate a pressure differential between the proximal and distal pressures, identify a suitable diagnostic window for performing a pressure differential calculation without administering a hyperemic agent to the patient, calculate a pressure differential during the identified diagnostic window, and/or combinations thereof.

Figure 9:
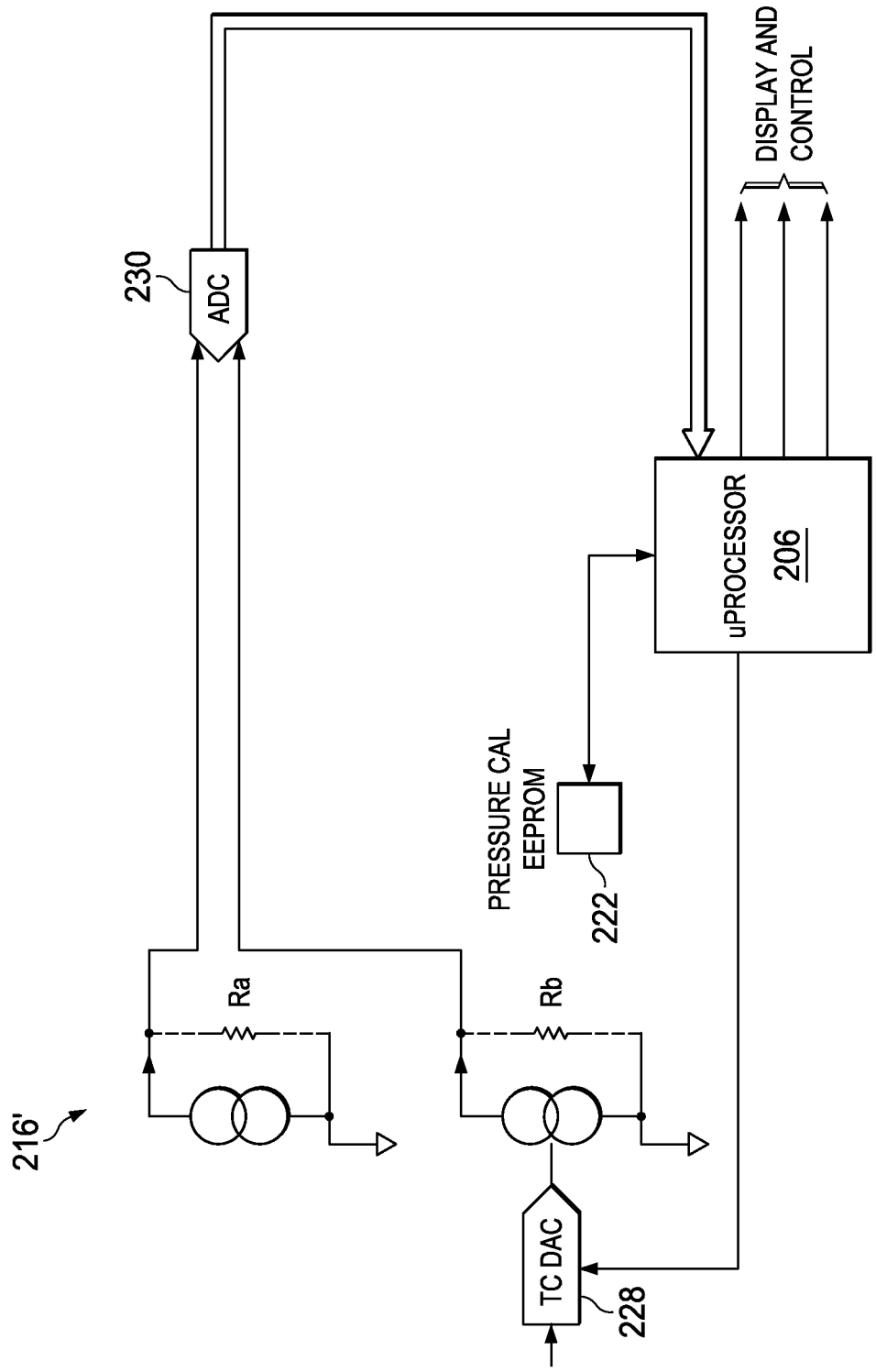
FIG. 9 is a diagrammatic, schematic view of a portion of the interface device of FIG. 7 similar to that of FIG. 8, but illustrating another embodiment of the present disclosure.

Referring now to FIG. 9, shown therein is a schematic of a portion the interface 170 according to another exemplary embodiment of the present disclosure. In particular, FIG. 9 shows a schematic of an exemplary embodiment of signal conditioning portion 216' of the interface 170. In that regard, the signal condition portion 216' is configured to condition signals received from the distal pressure measurement device. The signal conditioning portion 216' provides the excitation and amplification required for the distal pressure measurement device's pressure sensors, Ra and Rb, which collective form distal pressure sensing component 191 in some instances. The distal pressure signal from the pressure sensors, Ra and Rb, is digitized with a two-channel Analog to Digital Converter 230, ADC, and sent to the microprocessor 206 for the gain, offset, and/or temperature compensation. Calibration coefficients provided by the distal pressure measurement device utilizing an EPROM 222 in the device connector, for example, are read to adjust the gain, offset, and/or temperature sensitivity for the device. The read values are used by the microprocessor 206 to control the gain, offset, and/or temperature compensation. Firmware within the microprocessor is utilized to control these parameters in some instances. The microprocessor 206 can then display the distal pressure, display a waveform of the distal pressure, or utilize the distal pressure or the distal pressure waveform for additional calculations. For example, in some instances the microprocessor utilizes the distal pressure and/or distal pressure waveform with the proximal pressure and/or proximal pressure waveform to calculate FFR, calculate a pressure differential between the proximal and distal pressures, identify a suitable diagnostic window for performing a pressure differential calculation without administering a hyperemic agent to the patient, calculate a pressure differential during the identified diagnostic window, and/or combinations thereof. Accordingly, the signal conditioning portion 216' of FIG. 9 provides similar functionality to the signal conditioning device 216 of FIG. 8, but without the need for the three Digital to Analog Converters (DACs) 224, 226, and 228.

Referring again to FIG. 7, the interface 170 is also configured to output the distal pressure signal to an input 193 of a computing device. In that regard, the microprocessor 206 provides a digitized signal to an additional set of DACs in the distal output circuitry 218 that modulate the excitation of the hemo system to provide a proportional distal waveform of the distal pressure voltage back to the hemo system through output 192. In some embodiments, the scaled voltage returned is the same as a standard proximal pressure transducer, 5 µV/Vexc/mmHg, per the AAMI standards. The output stage 218 modulates the external excitation of the hemo system to provide a duplicate wave shape, or a DC Voltage, scaled to 5 µV/Vexc/mmHg, per AAMI standards for aortic transducers of the distal pressure for the hemo system. Accordingly, by outputting the distal pressure signal through output 192 and the proximal pressure signal through output 198, both proximal and distal pressures can then be observed on the hemo system's display using the hemo system's standard low-level inputs.

Figure 10:
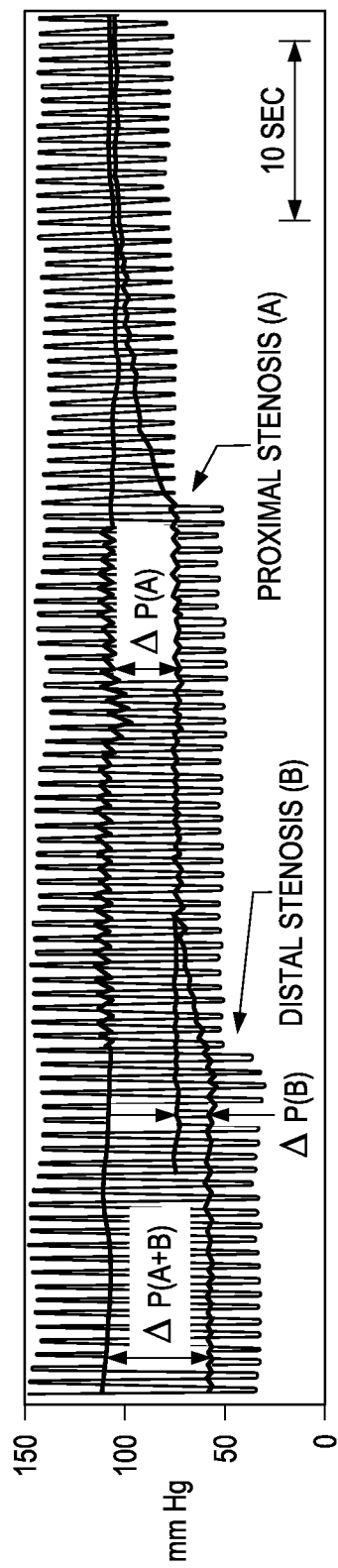
FIG. 10 is a graphical representation of proximal and distal pressure measurements over time during a pullback of a pressure sensing device obtaining the distal pressure measurements according to an embodiment of the present disclosure.
Figure 11:
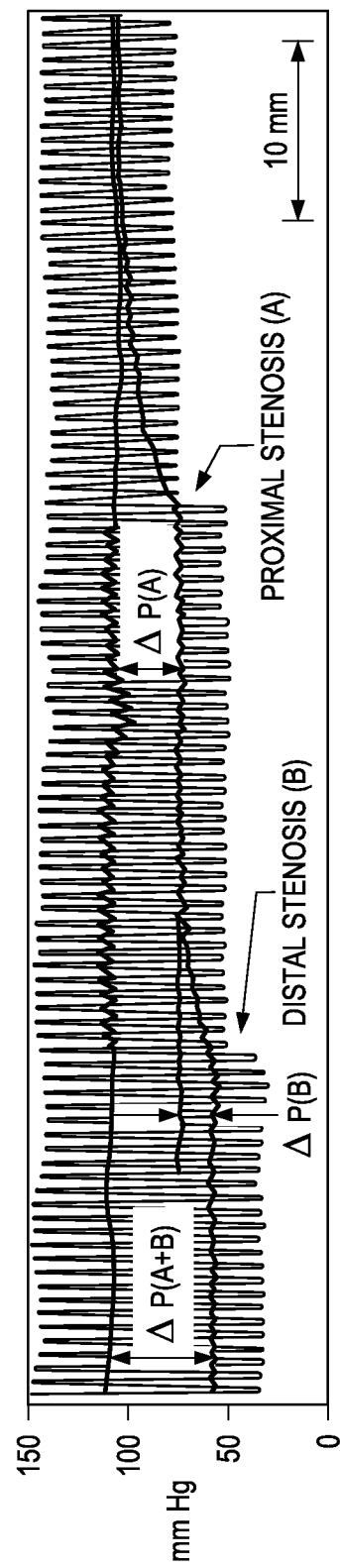
FIG. 11 is a graphical representation of proximal and distal pressure measurements during the pullback of the pressure sensing device obtaining the distal pressure measurements as shown in FIG. 10, but illustrating the proximal and distal pressure measurements relative to a distance according to an embodiment of the present disclosure.

As noted above, the interface 170 uses the proximal and distal pressure data received from the instruments to calculate and display information that can be useful in the evaluation of the vessel and, in particular, evaluation of a stenosis of the vessel. In some instances, the interface is configured to calculate and display FFR or other pressure ratio. For an FFR measurement, the microprocessor first normalizes the distal pressure to the aortic pressure. The difference or ratio between the distal and aortic pressures is utilized to determine FFR or pressure ratio. Further, in some instances the FFR or pressure ratio is calculated as at least the pressure sensing element of instrument 152 is moved through the vessel. Accordingly, in some instances the FFR or pressure ratio is tracked relative to movement of the pressure sensing element of instrument 152, for example, based on time or distance. To that end, information about the movement of the pressure sensing element of instrument 152 relative to the vessel and/or instrument 176 is obtained based on the motion, and associated timing of such motion, imparted by the pullback device 171. By correlating the difference or ratio between the two pressures to the movement associated with the pullback, a pressure ratio map or visual representation of the vessel can be created. For example, FIG. 10 provides a graphical representation of proximal and distal pressure measurements over time during a pullback of instrument 152 according to an embodiment of the present disclosure. FIG. 11 provides a graphical representation of the proximal and distal pressure measurements during the pullback of the instrument 152 of FIG. 10, but illustrates the proximal and distal pressure measurements relative to a distance according to an embodiment of the present disclosure. The resultant FFR or pressure ratio data (and associated positional/timing information) is stored in memory for later retrieval and/or shown on a display in real time.

In some embodiments the interface 170 includes user-controlled buttons, such as buttons 184 shown in FIGS. 4-6. In one particular embodiment, one of the buttons causes the microprocessor to 'normalize' the distal pressure measurement to the proximal pressure measurement. This is typically performed with the pressure sensing components 191 and 196 positioned in close proximity to one another within the patient such that they are subjected to similar pressures. In some instances, this calibration is performed proximal of the lesion and before the distal pressure sensing component 191 is advanced distally beyond the lesion. After the distal pressure sensing component 191 is placed beyond the suspect lesion actuation of another button causes the microprocessor 206 to calculate the ratio of the distal pressure to the proximal pressure, which provides an FFR value or pressure differential. In that regard, in some implementations the button is pressed by a user at a precise moment during hyperemia based on observation of the proximal and distal waveforms, which may be displayed on a separate device (e.g., a display of the hemo system) or displayed on display 182 of interface 170. Alternatively, the determination of the appropriate moment for the FFR calculation can be done automatically by the microprocessor 206. In that regard, in some instances the FFR calculation is performed at a point coinciding with the peak difference between the distal and proximal (aortic) pressures. In some embodiments, a pressure differential is calculated during a diagnostic window without application of a hyperemic agent, as discussed below. In such embodiments, the pressure measurements and/or the pressure differential may be displayed continuously. Further, in some instances a user-controlled button is utilized to start a pullback. In particular, actuation of the user-controlled button initiates the pullback device 171. In some instances, a single button is utilized to both initiate a pullback sequence and cause the microprocessor 206 to calculate the ratio of the distal pressure to the proximal pressure.

In some instances the interface 170 is configured to provide pressure measurements and/or pressure differentials based on evaluation techniques as described in one or more of UK Patent Application Publication No. GB 2479340 A, filed Mar. 10, 2010 and titled "METHOD AND APPARATUS FOR THE MEASUREMENT OF A FLUID FLOW RESTRICTION IN A VESSEL", UK Patent Application No. GB1100137.7, filed Jan. 6, 2011 and titled "APPARATUS AND METHOD OF ASSESSING A NARROWING IN A FLUID FILLED TUBE", U.S. Provisional Patent Application No. 61/525,739, filed on Aug. 20, 2011 and titled "DEVICES, SYSTEMS AND METHODS FOR ASSESSING A VESSEL," and U.S. Provisional Patent Application No. 61/525,736, filed on Aug. 20, 2011 and titled "DEVICES, SYSTEMS, AND METHODS FOR VISUALLY DEPICTING A VESSEL AND EVALUATING TREATMENT OPTIONS," each of which is hereby incorporated by reference in its entirety.

In some embodiments, the interface 170 is utilized to calculate and display FFR in a traditional FFR procedure where the patient is administered a hyperemic agent. In other embodiments, the interface 170 is utilized to calculate a pressure differential similar to FFR (i.e., the ratio of distal pressure to proximal pressure) but without the use of a hyperemic agent, including during a pullback in some implementations. In that regard, a suitable diagnostic window for making such calculations must be determined and/or identified to have a useful measurement. The diagnostic window for evaluating differential pressure across a stenosis without the use of a hyperemic agent in accordance with the present disclosure may be identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

In some embodiments, the determination of the diagnostic window and/or the calculation of the pressure differential are performed in approximately real time or live to identify the diagnostic window and calculate the pressure differential. In that regard, calculating the pressure differential in "real time" or "live" within the context of the present disclosure is understood to encompass calculations that occur within 10 seconds of data acquisition. It is recognized, however, that often "real time" or "live" calculations are performed within 1 second of data acquisition. In some instances, the "real time" or "live" calculations are performed concurrent with data acquisition. In some instances the calculations are performed by a processor in the delays between data acquisitions. For example, if data is acquired from the pressure sensing devices for 1 ms every 5 ms, then in the 4 ms between data acquisitions the processor can perform the calculations. It is understood that these timings are for example only and that data acquisition rates, processing times, and/or other parameters surrounding the calculations will vary. In other embodiments, the pressure differential calculation is performed 10 or more seconds after data acquisition. For example, in some embodiments, the data utilized to identify the diagnostic window and/or calculate the pressure differential are stored for later analysis.

In some instances, the diagnostic window is selected by identifying a portion of the cardiac cycle corresponding to a time period in which the change in velocity (i.e., dU) fluctuates around zero. Time periods where the change in velocity is relatively constant and approximately zero (i.e., the speed of the fluid flow is stabilized) are suitable diagnostic windows for evaluating a pressure differential across a stenosis of a vessel without the use of a hyperemic agent in accordance with the present disclosure. In that regard, in a fluid flow system, the separated forward and backward generated pressures are defined by:

$$dP_+ = \frac{1}{2}(dP + \rho c dU) \text{ and } dP_- = \frac{1}{2}(dP - \rho c dU),$$

where dP is the differential of pressure, ρ is the density of the fluid within the vessel, c is the wave speed, and dU is the differential of flow velocity. However, where the flow velocity of the fluid is substantially constant, dU is approximately zero and the separated forward and backward generated pressures are defined by:

$$dP_+ = \frac{1}{2}(dP + \rho c(0)) = \frac{1}{2}dP \text{ and } dP_- = \frac{1}{2}(dP - \rho c(0)) = \frac{1}{2}dP.$$

In other words, during the time periods where dU is approximately zero, the forward and backward generated pressures are defined solely by changes in pressure.

Accordingly, during such time periods the severity of a stenosis within the vessel can be evaluated based on pressure measurements taken proximal and distal of the stenosis. In that regard, by comparing the forward and/or backward generated pressure distal of a stenosis to the forward and/or backward generated pressure proximal of the stenosis, an evaluation of the severity of the stenosis can be made. For example, the forward-generated pressure differential can be calculated as $$\frac{dP_{+distal}}{dP_{+proximal}},$$

while the backward-generated pressure differential can be calculated as $$\frac{dP_{-distal}}{dP_{-proximal}}.$$

In the context of the coronary arteries, a forward-generated pressure differential is utilized to evaluate a stenosis in some instances. In that regard, the forward-generated pressure differential is calculated based on proximally originating (i.e., originating from the aorta) separated forward pressure waves and/or reflections of the proximally originating separated forward pressure waves from vascular structures distal of the aorta in some instances. In other instances, a backward-generated pressure differential is utilized in the context of the coronary arteries to evaluate a stenosis. In that regard, the backward-generated pressure differential is calculated based on distally originating (i.e., originating from the microvasculature) separated backward pressure waves and/or reflections of the distally originating separated backward pressure waves from vascular structures proximal of the microvasculature.

In yet other instances, a pressure wave is introduced into the vessel by an instrument or medical device. In that regard, the instrument or medical device is utilized to generate a proximally originating forward pressure wave, a distally originating backward pressure wave, and/or combinations thereof for use in evaluating the severity of the stenosis. For example, in some embodiments an instrument having a movable membrane is positioned within the vessel. The movable membrane of the instrument is then activated to cause movement of the membrane and generation of a corresponding pressure wave within the fluid of the vessel. Based on the configuration of the instrument, position of the membrane within the vessel, and/or the orientation of the membrane within the vessel the generated pressure wave(s) will be directed distally, proximally, and/or both. Pressure measurements based on the generated pressure wave(s) can then be analyzed to determine the severity of the stenosis.

There are a variety of signal processing techniques that can be utilized to identify time periods where the change in velocity is relatively constant and approximately zero, including using a differential, first derivative, second derivative, and/or third derivative of the velocity measurement are utilized. For example, identifying time periods during the cardiac cycle where the first derivative of velocity is relatively constant and approximately zero allows the localization of time periods where velocity is relatively constant. Further, identifying time periods during the cardiac cycle where the second derivative of velocity is relatively constant and approximately zero allows the localization of a time period where acceleration is relatively constant and near zero, but not necessarily zero.

While examples of specific techniques for selecting a suitable diagnostic window have been described above, it is understood that these are exemplary and that other techniques may be utilized. In that regard, it is understood that the diagnostic window is determined using one or more techniques selected from: identifying a feature of a waveform or other data feature and selecting a starting point relative to the identified feature (e.g., before, after, or simultaneous with the feature); identifying a feature of a waveform or other data feature and selecting an ending point relative to the identified feature (e.g., before, after, or simultaneous with the feature); identifying a feature of a waveform or other data feature and selecting a starting point and an ending point relative to the identified feature; identifying a starting point and identifying an ending point based on the starting point; and identifying an ending point and identifying a starting point based on the ending point. Additional details of techniques for selecting a suitable diagnostic window are described in U.S. Provisional Patent Application No. 61/525,739, filed on Aug. 20, 2011 and titled "DEVICES, SYSTEMS AND METHODS FOR ASSESSING A VESSEL," which is hereby incorporated by reference in its entirety. In that regard, it is understood that the interface 170 may be programmed to determine one or more diagnostic windows based on the techniques described in the present disclosure, including those incorporated by reference, and/or include one or more hardware features configured to identify one or more diagnostic windows based on the techniques described in the present disclosure, including those incorporated by reference.

Further, for a variety of reasons the proximal pressure measurements and the distal pressure measurements received by the interface 170 are not temporally aligned in some instances. For example, during data acquisition, there will often be a delay between the distal pressure measurement signals and the proximal pressure measurement signals due to hardware signal handling differences between the instrument(s) utilized to obtain the measurements. In that regard, the differences can come from physical sources (such as cable length and/or varying electronics) and/or can be due to signal processing differences (such as filtering techniques). The resulting delay between the signals is between about 5 ms and about 150 ms in some instances. Because individual cardiac cycles may last between about 500 ms and about 1000 ms and the diagnostic window may be a small percentage of the total length of the cardiac cycle, longer delays between the proximal and distal pressure measurement signals can have a significant impact on alignment of the pressure data for calculating a pressure differential for a desired diastolic window of a cardiac cycle.

As a result, in some instances, it is necessary to shift one of the proximal and distal pressures relative to the other of the distal and proximal pressures in order to temporally align the pressure measurements. For example, a portion of the distal pressure measurement or proximal pressure measurement may be shifted to be temporally aligned with a corresponding portion of the proximal pressure measurement or distal pressure measurement, respectively, coinciding with the diagnostic window. While a shift of only a portion of the distal or proximal pressure measurement associated with the diagnostic window is utilized in some instances, in other instances all or substantially all of the proximal and distal pressures are aligned before the portions corresponding to a selected diagnostic window are identified.

Alignment of all or portion(s) of the proximal and distal pressures is accomplished using a hardware approach in some instances. For example, one or more hardware components are positioned within the communication path of the proximal pressure measurement, the distal pressure measurement, and/or both to provide any necessary delays to temporally align the received pressure signals. In some instances, these hardware components are positioned within the interface 170. In other instances, alignment of all or portion(s) of the proximal and distal pressures is accomplished using a software approach. For example, a cross-correlation function or matching technique is utilized to align the cardiac cycles in some embodiments. In other embodiments, the alignment is based on a particular identifiable feature of the cardiac cycle, such as an ECG R-wave or a pressure peak. Additionally, in some embodiments alignment is performed by a software user where adjustments are made to the delay time of at least one of the proximal and distal pressures until the cardiac cycles are visually aligned to the user. A further technique for aligning the signals is to apply a synchronized timestamp at the point of signal acquisition. Further, in some instances combinations of one or more of hardware, software, user, and/or time-stamping approaches are utilized to align the signals.

Regardless of the manner of implementation, several approaches are available for the aligning the proximal and distal pressure measurement signals. In some instances, each individual distal pressure measurement cardiac cycle is individually shifted to match the corresponding proximal pressure measurement cardiac cycle. In other instances, an average shift for a particular procedure is calculated at the beginning of the procedure and all subsequent cardiac cycles during the procedure are shifted by that amount. This technique requires little processing power for implementation after the initial shift is determined, but can still provide a relatively accurate alignment of the signals over the course of a procedure because the majority of the signal delay is due to fixed sources that do not change from patient to patient or within the procedure. In yet other instances, a new average shift is calculated each time that the proximal and distal pressure signals are normalized to one another during a procedure. In that regard, one or more times during a procedure the sensing element utilized for monitoring pressure distal of the stenosis is positioned adjacent the sensing element utilized for monitoring pressure proximal of the stenosis such that both sensing elements should have the same pressure reading. If there is a difference between the pressure readings, then the proximal and distal pressure signals are normalized to one another. As a result, the subsequently obtained proximal and distal pressure measurements are more consistent with each other and, therefore, the resulting pressure differential calculations are more accurate.

With the proximal and distal pressure measurements aligned, the pressure differential for the diagnostic window is calculated. In some instances, the pressure differential is calculated using average values for the proximal and distal pressure measurements across the diagnostic window. The pressure differential calculations of the present disclosure are performed for a single cardiac cycle, in some instances. In other instances, the pressure differential calculations are performed for multiple cardiac cycles. In that regard, accuracy of the pressure differential can be improved by performing the pressure differential calculations over multiple cardiac cycles and averaging the values and/or using an analysis technique to identify one or more of the calculated values that is believed to be most and/or least accurate.

One advantage of the techniques of the present disclosure for identifying diagnostic windows and evaluating pressure differentials is the concept of "beat matching". In that regard, the proximal and distal waveforms for the same cardiac cycle are analyzed together with no averaging or individual calculations that span more than a single cardiac cycle. As a result, interruptions in the cardiac cycle (such as ectopic heartbeats) equally affect the proximal and distal recordings. As a result, these interruptions that can be detrimental to current FFR techniques have minor effect on the techniques of the present disclosure. Further, in some embodiments of the present disclosure, the effect of interruptions in the cardiac cycle and/or other irregularities in the data is further minimized and/or mitigated by monitoring the pressure differential calculations to detect these anomalies and automatically exclude the impacted cardiac cycles.

In one particular embodiment, pressure differential is calculated on two sequential cardiac cycles and the individual pressure differential values are averaged. The pressure differential of a third cycle is then calculated. The average value of the pressure differentials is compared to the average pressure differential using three cycles. If the difference between the averages is below a predetermined threshold value, then the calculated value is considered to be stable and no further calculations are performed. For example, if a threshold value of 0.001 is used and adding an additional cardiac cycle changes the average pressure differential value by less than 0.001, then the calculation is complete. However, if the difference between the averages is above the predetermined threshold value, then the pressure differential for a fourth cycle is calculated and a comparison to the threshold value is performed. This process is repeated iteratively until the difference between the averages of cardiac cycle N and cardiac cycle N+1 is below the predetermined threshold value. As the pressure differential value is typically expressed to two decimal places of precision (such as 0.80), the threshold value for completing the analysis is typically selected to be small enough that adding a subsequent cardiac cycle will not change the pressure differential value. For example, in some instances the threshold value is selected to be between about 0.0001 and about 0.05.

In some instances, the level of confidence calculation has different thresholds depending on the degree of stenosis and/or an initial calculated pressure differential value. In that regard, pressure differential analysis of a stenosis is typically based around a cutoff value(s) for making decisions as to what type of therapy, if any, to administer. Accordingly, in some instances, it is desirable to be more accurate around these cutoff points. In other words, where the calculated pressure differential values are close to a cut-off, a higher degree of confidence is required. For example, if the cutoff for a treatment decision is at 0.80 and the initial calculated pressure differential measurement is between about 0.75 and about 0.85, then a higher degree of confidence is needed than if the initial calculated pressure differential measurement is 0.40, which is far from the 0.80 cutoff point. Accordingly, in some instances the threshold value is at least partially determined by the initial calculated pressure differential measurement. In some instances, the level of confidence or stability of the calculated pressure differential is visually indicated to user via a software interface.

Because pressure differential can be calculated based on a single cardiac cycle in accordance with the present disclosure, a real-time or live pressure differential calculation can made while the distal pressure measuring device is moved through the vessel. Accordingly, in some instances the system includes at least two modes: a single-cardiac-cycle mode that facilitates pressure differential calculations while moving the distal pressure measuring device through the vessel and a multi-cardiac-cycle mode that provides a more precise pressure differential calculation at a discrete location. In one embodiment of such a system, the interface 170 is configured to provide the live pressure differential value until the distal pressure measuring device is moved to the desired location and a measurement button is selected and/or some other actuation step is taken to trigger the multi-cardiac-cycle mode calculation.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An interface for intravascular pressure sensing devices, comprising:
   a single housing;
   a first input connector configured to receive a distal pressure signal generated by a first pressure-monitoring element of a distal pressure sensing guidewire comprising a proximal portion and a distal portion, wherein the pressure-monitoring element is coupled to the distal portion of the distal pressure sensing guidewire;
   a first output connector configured to output the distal pressure signal over a first communication link to a hemodynamic system in a format useable by the hemodynamic system;
   a second input connector configured to receive a proximal pressure signal generated by a second pressure-monitoring element coupled to a proximal pressure sensing device;
   a second output connector different from the first output connector and configured to output the proximal pressure signal over a second communication link to the hemodynamic system in a format useable by the hemodynamic system;
   a processor in communication with the first input connector, the first output connector, the second input connector, and the second output connector, the processor configured to calculate a pressure differential between a distal pressure and a proximal pressure based on the received distal pressure signal generated by the first pressure-monitoring element and the received proximal pressure signal generated by the second pressure-monitoring element, wherein the received distal pressure signal and the received proximal pressure signal are obtained as a pullback device translates the distal pressure sensing guidewire relative to the proximal pressure sensing device;
   a first amplifier communicatively disposed between the second input connector and the processor and configured to sample the proximal pressure signal, wherein the processor is in communication with the second input connector and the second output connector via the first amplifier; and
   a display in communication with the processor and configured to display the pressure differential calculated by the processor simultaneously with a display of a relative position of the distal pressure sensing guidewire to the proximal pressure sensing device associated with the calculated pressure differential,
   wherein the first input connector, the first output connector, the second input connector, the second output connector, the processor, the first amplifier, and the display are coupled to the single housing, wherein the interface is separate from the hemodynamic system.

2. The interface of claim 1, wherein the housing has a width between 5 cm and 25 cm, a height between 5 cm and 25 cm, and a depth between 1 cm and 10 cm.

3. The interface of claim 1, wherein the proximal pressure sensing device is a pressure-sensing catheter.

4. The interface of claim 1, wherein the processor is communicatively coupled to the hemodynamic system of the interface via the first and second output connectors.

5. The interface of claim 1, wherein the single housing is sized and shaped to be handheld.

6. A system for evaluating a vascular stenosis, the system comprising:
   a distal pressure sensing guidewire sized and shaped for insertion into human vasculature, the distal pressure sensing guidewire comprising a proximal portion, a distal portion, and a first pressure-monitoring element coupled to the distal portion, wherein the first pressure-monitoring element is configured to generate a distal pressure signal representative of blood within the human vasculature while the distal pressure sensing guidewire is inserted into the human vasculature; and
   an interface comprising:
      a single housing;
      a first input connector configured to receive the distal pressure signal generated by the first pressure-monitoring element of the distal pressure sensing guidewire;
      a first output connector configured to output the distal pressure signal over a first communication link to a hemodynamic system in a format useable by the hemodynamic system;
      a second input connector configured to receive a proximal pressure signal generated by a second pressure-monitoring element coupled to a proximal pressure sensing device;
      a second output connector different from the first output connector and configured to output the proximal pressure signal over a second communication link to the hemodynamic system in a format useable by the hemodynamic system;
      a processor in communication with the first input connector, the first output connector, the second input connector, and the second output connector, the processor configured to calculate a pressure differential between a distal pressure and a proximal pressure based on the received distal pressure signal generated by the first pressure-monitoring element and the received proximal pressure signal generated by the second pressure-monitoring element, wherein the received distal pressure signal and the received proximal pressure signal are obtained as a pullback device translates the distal pressure sensing guidewire relative to the proximal pressure sensing device;

a first amplifier communicatively disposed between the second input connector and the processor and configured to sample the proximal pressure signal, wherein the processor is in communication with the second input connector and the second output connector via the first amplifier; and a display in communication with the processor and configured to display the pressure differential calculated by the processor simultaneously with a display of a relative position of the distal pressure sensing guidewire to the proximal pressure sensing device associated with the calculated pressure differential, wherein the first input connector, the first output connector, the second input connector, the second output connector, the processor, the first amplifier, and the display are coupled to the single housing, wherein the interface is separate from the hemodynamic system.

7. The system of claim 6, wherein the display is a touchscreen.

8. The system of claim 6, wherein the display is further configured to display the proximal pressure and the distal pressure.

9. The system of claim 6, further comprising the proximal pressure sensing device, wherein the proximal pressure sensing device is a pressure-sensing catheter.

10. The system of claim 9, wherein the second pressure-monitoring element is disposed at a proximal portion of the pressure-sensing catheter.

11. The system of claim 10, wherein the pressure-sensing catheter comprises a fluid column extending along a length of the pressure-sensing catheter, wherein the further pressure-monitoring element comprises a fluid column sensor.

12. The system of claim 11, further comprising:
a hemostasis valve fluidly coupled to the fluid column of the catheter;
a manifold fluidly coupled to the hemostasis valve; and
tubing extending between at least one of the fluid column sensor, the hemostasis valve, or the manifold,
wherein the fluid column sensor is fluidly coupled to the fluid column of the catheter via the hemostasis valve, the manifold, or the tubing.

13. The system of claim 9,
wherein the pressure-sensing catheter comprises a lumen,
wherein the distal pressure sensing guide wire is configured to obtain the distal pressure while the pressure-sensing guide wire extends through the lumen of the pressure-sensing catheter.

14. The system of claim 6, wherein the interface is communicatively disposed between the hemodynamic system, and the distal pressure sensing guidewire and the proximal pressure sensing device.

15. The system of claim 6, further comprising:
the pullback device, wherein the pullback device is configured to interface with a proximal portion of the distal pressure sensing guidewire to translate the distal pressure sensing guidewire from a first position to a second position relative to the proximal pressure sensing device.

16. The system of claim 6, further comprising a processing system that is separate from the interface and the hemodynamic system.

17. The system of claim 6, further comprising a processing system that comprises the hemodynamic system.

18. The system of claim 6,
wherein the processor is configured to calculate the pressure differential between the distal pressure and the proximal pressure for each cardiac cycle of a patient,
wherein the received distal pressure signal and the received proximal pressure signal are obtained during a diagnostic window of each cardiac cycle, and
wherein a starting point of the diagnostic window is selected based on at least one of the received proximal pressure signal or the received distal pressure signal and an ending point of the diagnostic window is selected based on at least one of the received proximal pressure signal or the received distal pressure signal such that the diagnostic window encompasses only a portion of each cardiac cycle of the patient.

19. The system of claim 6, wherein the interface further comprises a second amplifier communicatively disposed between the second input connector and the processor and configured to sample an excitation voltage passed from the hemodynamic system to the proximal pressure sensing device, wherein the processor is in communication with the second input connector and the second output connector via the second amplifier, wherein the single housing comprises the second amplifier.

20. The system of claim 19, further comprising a first conductor and a second conductor in electrical communication with the second pressure-monitoring element and the hemodynamic system,
wherein the first conductor and the second conductor are configured to carry the proximal pressure signal from the second pressure-monitoring element to the hemodynamic system,
wherein the first amplifier is configured to sample the proximal pressure signal from the first conductor and the second conductor.

21. The system of claim 20, further comprising a third conductor and a fourth conductor in electrical communication with the second pressure-monitoring element and the hemodynamic system,
wherein the third conductor and the fourth conductor are configured to carry the excitation signal from the hemodynamic system to the second pressure-monitoring element,
wherein the second amplifier is configured to sample the excitation signal from the third conductor and the fourth conductor.

22. The system of claim 21, wherein the processor is in communication with the first amplifier and the second amplifier such that the processor is configured to calculate the proximal pressure based on the proximal pressure signal and the excitation signal.

23. The system of claim 19, wherein the interface further comprises circuitry in communication with the processor, wherein the circuitry is configured to modulate the distal pressure signal based on the excitation signal to generate an output transmitted to the hemodynamic system via the first output connector.

24. The system of claim 6, wherein between the distal pressure sensing guidewire and the hemodynamic system, the distal pressure signal passes sequentially through the first input connector, a first analog to digital converter, the processor, a digital to analog converter, and the first output connector.

25. The system of claim 6, wherein between the proximal pressure sensing device and the hemodynamic system, the proximal pressure signal passes sequentially through the second input connector and the second output connector.

26. The system of claim 6,
wherein the distal pressure sensing guide wire comprises a shaft and a housing coupled to the shaft at the distal portion,
wherein the housing contains the first pressure-monitoring element,
wherein the distal portion terminates at a distal tip, and
wherein the housing is spaced from the distal tip.

27. The system of claim 26, wherein the first pressure-monitoring element comprises at least one of a transducer, a piezo-resistive pressure sensor, a piezo-electric pressure sensor, a capacitive pressure sensor, an electromagnetic pressure sensor, a fluid column, or an optical pressure sensor.

28. The system of claim 6,
wherein the first input connector, the first output connector, the second input connector, and the second output connector are each secured to the single housing,
wherein the connectors are distinct and spaced from one another.

29. The system of claim 6, further comprising the hemodynamic system.

* * * * *